United States Patent
Puleo et al.

(10) Patent No.: US 11,551,796 B2
(45) Date of Patent: Jan. 10, 2023

(54) SYSTEMS AND METHODS FOR PRESCRIPTION AND DOSING OF THERAPEUTIC STIMULI USING RECORDED GUARANTEES

(71) Applicant: General Electric Company, Schenectady, NY (US)

(72) Inventors: Christopher Puleo, Niskayuna, NY (US); Benjamin Beckmann, Niskayuna, NY (US); Victor Abate, Albany, NY (US); John Freer, Niskayuna, NY (US); David Vernooy, Niskayuna, NY (US); Jeffrey Ashe, Gloversville, NY (US)

(73) Assignee: General Electric Company, Niskayuna, NY (US)

( * ) Notice: Subject to any disclaimer, the term of this patent is extended or adjusted under 35 U.S.C. 154(b) by 66 days.

(21) Appl. No.: 16/456,708

(22) Filed: Jun. 28, 2019

(65) Prior Publication Data
US 2020/0411151 A1    Dec. 31, 2020

(51) Int. Cl.
*G16H 20/10*    (2018.01)
*G16H 10/60*    (2018.01)

(52) U.S. Cl.
CPC ............ *G16H 20/10* (2018.01); *G16H 10/60* (2018.01)

(58) Field of Classification Search
CPC ............................ G16H 20/10; G16H 10/60
USPC ........................................................ 705/2–3
See application file for complete search history.

(56) References Cited

U.S. PATENT DOCUMENTS

| | | | |
|---|---|---|---|
| 8,092,224 | B2 | 1/2012 | Walker et al. |
| 10,061,899 | B2 | 8/2018 | Miller et al. |
| 2011/0066083 | A1 | 3/2011 | Tosaya et al. |
| 2016/0213924 | A1 | 7/2016 | Coleman et al. |
| 2018/0130034 | A1 | 5/2018 | Taylor et al. |
| 2018/0144817 | A1* | 5/2018 | Lofgren ............... G16H 10/60 |
| 2018/0165416 | A1 | 6/2018 | Saxena et al. |
| 2018/0267700 | A1 | 9/2018 | Kaditz et al. |

(Continued)

FOREIGN PATENT DOCUMENTS

| | | |
|---|---|---|
| KR | 101882207 B1 | 7/2018 |
| KR | 101964733 B1 | 4/2019 |

(Continued)

OTHER PUBLICATIONS

Sood et al., "The Flow of Money through the pharmaceutical," USC Schaeffer for Health Policy and Economics, Jun. 2017, 7 pages.
Azaria, Asaph, et al.; "MedRec: Using Blockchain for Medical Data Access and Permission Management", 2016 2nd International Conference on Open and Big Data (OBD), pp. 25-30, Austria, Aug. 22-24, 2016.

(Continued)

*Primary Examiner* — Jonathan Durant
*Assistant Examiner* — Benjamin L. Hanks
(74) *Attorney, Agent, or Firm* — Fletcher Yoder P.C.

(57) ABSTRACT

Systems and methods for management of a distributed ledger including prescription information are disclosed. An example apparatus includes a processor and a logical data structure to configure a device according to an electronic prescription defining an action for a patient, the electronic prescription organized as record(s) in a distributed ledger and processible by the device to apply the action to the patient. The electronic prescription is to cause the device to at least: configure the device to apply the action to the patient; validate the action for the patient using the distributed ledger; and propagate a record of the action to the distributed ledger.

20 Claims, 22 Drawing Sheets

(56) References Cited

U.S. PATENT DOCUMENTS

| | | | | |
|---|---|---|---|---|
| 2019/0198144 A1* | 6/2019 | Blackley | ................ | G16H 20/10 |
| 2019/0206536 A1* | 7/2019 | Hausman | .............. | H04L 9/3297 |
| 2019/0312734 A1* | 10/2019 | Wentz | .................. | H04L 9/3247 |

FOREIGN PATENT DOCUMENTS

| | | | | |
|---|---|---|---|---|
| WO | 2015175722 A1 | 11/2015 | | |
| WO | 2017221052 A1 | 12/2017 | | |
| WO | 2018081826 | 5/2018 | | |
| WO | WO 2018/081826 | * | 5/2018 | |
| WO | WO-2018081826 A1 * | 5/2018 | ......... | A61B 5/04001 |
| WO | 2019045737 | 3/2019 | | |
| WO | 2019045739 | 3/2019 | | |
| WO | 2018160228 | 9/2019 | | |

OTHER PUBLICATIONS

Shubbar, Safa, "Ultrasound Medical Imaging Systems Using Telemedicine and Blockchain for Remote Monitoring of Responses to Neoadjuvant Chemotherapy in Women's Breast Cancer: Concept and Implementation", Electronic Theses & Dissertations Center, pp. 1-132, 2017.

Kaur, Harleen, et al.; "A Proposed Solution and Future Direction for Blockchain-Based Heterogeneous Medicare Data in Cloud Environment", Journal of Medical Systems, vol. 42, Issue: 8, Aug. 2018.

Rahman, Md. Abdur, et al.; "Blockchain-based Mobile Edge Computing Framework for Secure Therapy Applications", IEEE Access, Nov. 14, 2018.

International Search Report and Written Opinion for PCT Application No. PCT/US2020/039921 dated Oct. 22, 2020, 10 pgs.

* cited by examiner

SYSTEMS AND METHODS FOR PRESCRIPTION AND DOSING OF THERAPEUTIC STIMULI USING RECORDED GUARANTEES

FIELD OF THE DISCLOSURE

This disclosure relates generally to improved prescription management and, more particularly, to improved systems and methods for distributed ledger management of prescription and dosing.

BACKGROUND

Prescription management is an important area vital for public health and patient treatment but rife with fraud and abuse as well as lack of consistency and transparency. Errors in prescriptions, lack of accountability or auditability, etc., plague the healthcare system, and an inability for third parties to evaluate prescription information contribute to societal problems such as the opioid epidemic. Additionally, in current systems, a pharmacy plays a key role in collecting funds and dispensing a prescription to a beneficiary. Without the pharmacy, the system breaks down and cannot provide prescriptions to patients.

BRIEF DESCRIPTION

Certain examples provide systems and methods for tracking and management of a distributed ledger including electronic prescription information.

Certain examples provide an apparatus including an energy application device, a pulse generator, a controller, and memory including a logical data structure to configure the apparatus according to an electronic prescription defining an action for a patient, the electronic prescription organized as one or more records in a distributed ledger and processible by the controller to apply the action to the patient. The electronic prescription is to, when processed by the controller, cause the controller to at least: configure the energy application device and the pulse generator to apply the action to the patient; validate the action for the patient using the distributed ledger; and propagate a record of the action to the distributed ledger.

Certain examples provide at least one computer-readable storage medium including a logical data structure to configure a device according to an electronic prescription defining an action for a patient, the electronic prescription organized as one or more records in a distributed ledger and processible by the device to apply the action to the patient and including instructions which, when executed, cause at least one processor to at least: configure the device to apply the action to the patient; validate the action for the patient using the distributed ledger; and propagate a record of the action to the distributed ledger.

Certain examples provide a computer-implemented method to configure a device according to an electronic prescription defining an action for a patient, the electronic prescription organized as one or more records in a distributed ledger and processible by the device to apply the action to the patient. The example method includes configuring, by at least one processor using the electronic prescription, the device to apply the action to the patient. The example method includes validating, by at least one processor using the electronic prescription, the action for the patient using the distributed ledger. The example method includes propagating, by the at least one processor using the electronic prescription, a record of the action to the distributed ledger.

BRIEF DESCRIPTION OF THE DRAWINGS

The figures are not scale. Wherever possible, the same reference numbers will be used throughout the drawings and accompanying written description to refer to the same or like parts.

DETAILED DESCRIPTION

Figure 1:
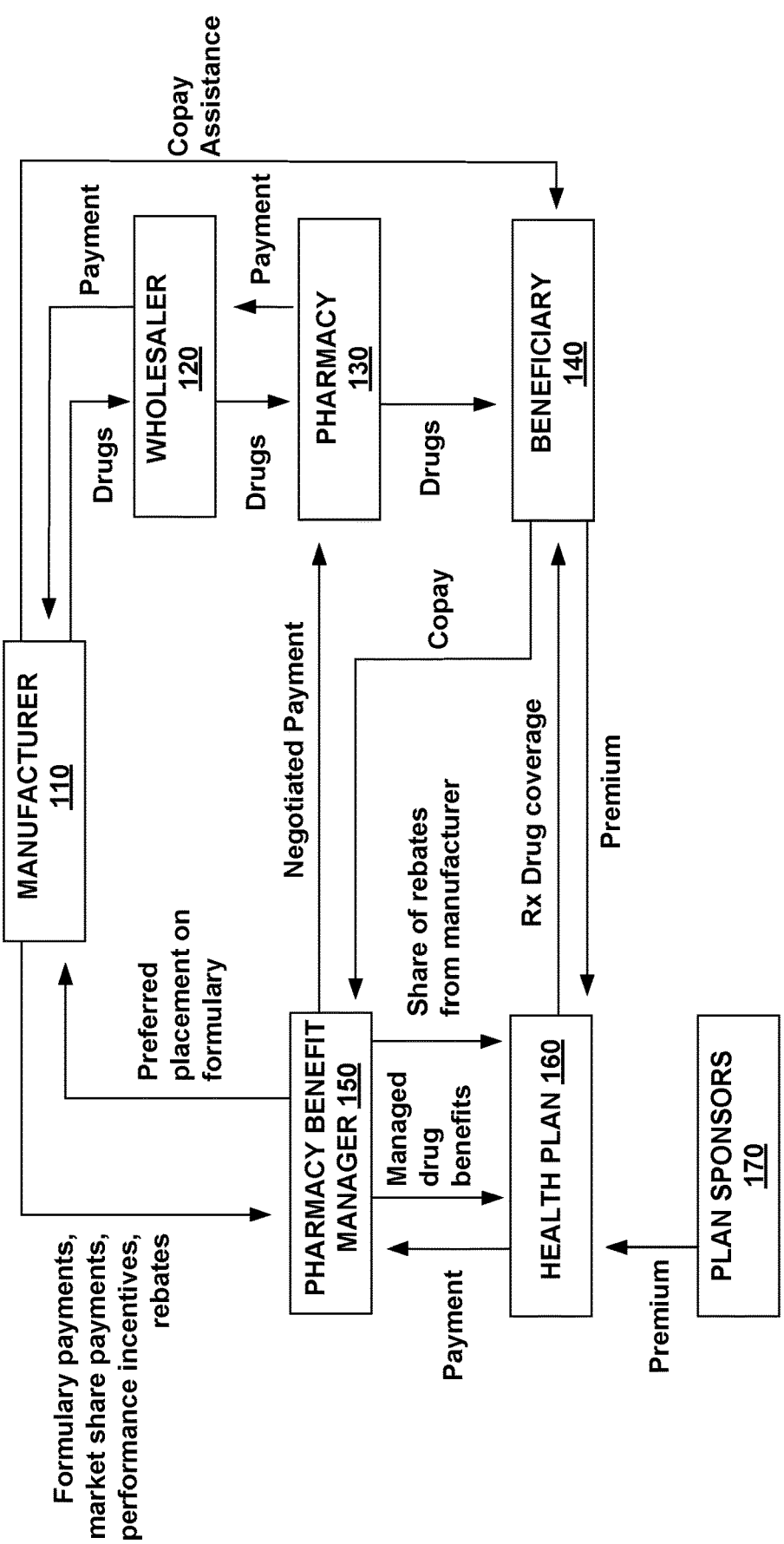
FIG. 1 depicts an example prescription ecosystem.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Prescriptions can be used to order, provide, and regulate therapeutic materials and/or treatment protocols to a patient in accordance with a treatment regimen, protocol, etc. Such therapeutic material can include pharmaceutical drugs, energy dosage, exercise regimen, dietary supplement, etc. Using an electronic prescription, ordering, paying, administering, and tracking of therapeutic materials can be dynamically managed and enhanced beyond existing prescription management capabilities.

For example, methods and systems disclosed and described herein provide secure recording of energy dose(s) administered to a patient for therapeutic purposes, using secure methods to validate the given dose(s). In certain examples, an energy device providing an energy stimulus to a patient's internal/external tissue modifies an electronic document (e.g., an entry or record in a blockchain or other distributed ledger, etc.) and can transmit the change via a network to one or more participating/connected systems (e.g., electronic medical record systems, health information systems, hospital information systems, prescription management systems, radiology information systems, enterprise archives, etc.) which can update and/or store an updated copy of the electronic document. For example, a dose log chain residing on the network and shared among all the nodes (e.g., devices, servers, other systems, etc.) on the network stores the dose information. A node on the network can verify a change of dosing and/or other therapeutic output made by other nodes and add a new block to the chain using one-way hashes, etc., to make the chain resistant to tampering. If an invalid block is detected, the system can send an auditing alert to the network. An audit log can be strongly resistant to tampering, providing reliable evidence for use in auditing patient compliance, therapeutic effectiveness, therapeutic device function, or patient/dose record keeping, for example.

Certain examples leverage a blockchain and/or other distributed ledger (e.g., "Dose Coin") to help guarantee information within a transaction between a healthcare provider and a patient/user of a non-invasive (or invasive) energy driven therapeutic machine and/or other treatment device. For example, a blockchain and/or other distributed ledger can be used to guarantee dosing from a therapeutic machine is communicated to other participants within a healthcare ecosystem.

In certain examples, data is stored and verified in association with energy delivery to a patient (e.g., an in-home system for energy delivery to the patient, etc.). Verification of person that is receiving doses can be done using biometric data (e.g., biometric data obtained for each dose, etc.), for example. For example, a digital pharmacy log of a patient and an associated number and/or other amount of doses of a prescription medication can be tracked using biometric data (e.g., including a variety of biometric data such as images obtained from a "dosing" machine verifying amount, type, time, recipient, etc.). Verification of a number of doses of a given prescription substance that an individual takes can be tracked for diagnosis and treatment, insurance/billing, addiction management, (e.g., do not allow addictions to develop), etc. Data can be stored as records or blocks in a distributed ledger, for example. The ledger can be accessible and/or retained by an electronic medical record system including the patient's record, a physician's monitoring application, an insurance company system and/or other payer/provider system, a pharmaceutical system, etc.

Records in the distributed ledger can be used to store patient compliance data, such as which patient is following a "dose" regimen most closely, etc. The record(s) can work with an electronic medical record system to compare monitored data to prescription and guideline and compare compliance/adherence to protocol, for example. Records in the distributed ledger can be used to store doctor prescription data, such as doctors are prescribing most effectively, etc. Records in the distributed ledger can be used to store effectiveness data, such as a physiological effect of a particular dose, etc. Records in the distributed ledger can be used to store an indication of hardware/therapy effectiveness, such as how well a machine performed in providing a dose to a patient. Records in the distributed ledger can be used to store dynamic dosing data to enable changing prescriptions based on physiological feedback measurements, for example.

In certain examples, additional verification of transactions and/or dosing can be performed based on sender and recipient of therapeutic dose information and/or other prescription information, etc. For example, additional verification can include using image recognition (e.g., of the patient's internal/external tissue) to verify dose based on patient, location, etc. Additional verification can include using tissue and/or physiological response to verify an amplitude or dose of energy applied by a therapy device, for example. Additional verification can include using feedback from one or more internal and/or external sensors that measure energy being applied to a patient, for example. In certain examples, other features, such as changes in blood flow and/or other physiological response, can be used as verification of dosing. Some or all of these measures can also be used in a consensus algorithm (e.g., including personal image recognition, etc.) to verify people involved dosing, for example. In certain examples, therapeutic hardware can also be tied to another electronic device, such as a cell phone, tablet computer, smart watch, etc., to use global position and/or other biometric data to tie a person to a device and verify dosing.

In certain examples, a distributed ledger prescription system can be internally facing to store information so that a therapeutic company knows how its own system is used. Alternatively or in addition, the distributed ledger prescription system can be externally facing so that the therapeutic company can provide dosing data to other healthcare players, such as insurance companies, etc., to allow value to be derived from dosing information. For example, this value can drive determination of different patient insurance premiums based on compliance to a prescribed therapeutic regimen, different insurance payouts for hospital systems that perform better at diagnosing correct energy application or dosing regimens, etc.

In certain examples, participants in such a block chain and/or other distributed ledger can include a patient, primary healthcare provider(s), therapy provider(s), hospital(s)/healthcare system(s), diagnostic/therapeutic equipment providers, insurer(s), insurance claim administrator/investigator(s), government/guiding agency(-ies), consumer company(-ies) that may impact patient health through provision of related or non-related products, other actor(s) in the healthcare space, etc. In certain examples, while a pharmacy system can be involved in the verification process, the pharmacy system is not required to play a role. Instead, a hospital and/or other patient health system can interact with a supplier to provide treatment material to a patient and track its dosage, use, refill, etc.

A therapeutic energy source and/or other neuromodulation material, chemical agent, other drug, etc., can be prescribed and applied to a patient as a normalizing agent for treatment of a patient condition such as epilepsy, pain, sensory deficit, organ control (e.g., bladder, bowel, and/or respiratory control, etc.), depression, Alzheimer's disease, stroke, other neural condition, etc. In certain examples, multiple systems are involved in the prescription, distribution, payment, and application of such an agent.

For example, FIG. 1 depicts an example prescription ecosystem 100 providing therapeutic material and/or other drugs and services for patient treatment in exchange for funds. As shown in the example of FIG. 1, a manufacturer system 110, such as a radiopharmaceutical manufacturer system, a drug manufacturer system, a medical device manufacturer system, and/or a sensor manufacturer system, etc., can provide a product, such as a radiopharmaceutical, a pharmaceutical, a medical device, and/or a sensor, etc., to a wholesaler system 120. For example, the manufacturer system 110 tracks a manufactured supply of goods and updates a record indicating that a good has been provided to a wholesaler associated with the wholesaler system 120. For example, an energy therapy device and/or associated material (e.g., chemical agent, radiopharmaceutical material, energy source, other drug, etc.) can be generated by the manufacturer system 110 and provided to the wholesaler system 120 to be sold and/or otherwise distributed to one or more beneficiaries 140 via a pharmacy system 130. Exchange of goods and payment in return for those goods is facilitated between the manufacturer system 110 and the wholesaler system 120 and between the wholesaler system 120 and the pharmacy system 130, for example.

However, in certain examples, one or both of the pharmacy system 130 and the wholesaler system 120 can be removed by instead working directly between the manufacturer system 110 and the beneficiary device 140. A benefit manager system 150, extracting information from a health plan data construct 160 having one or more plan sponsors 170, can trigger distribution of the prescription to the beneficiary system 140 as well as payment, rebate, etc., to the manufacturer system 110, with or without the wholesaler system 120 and/or the pharmacy system 130, for example. A record, such as a blockchain and/or other distributed ledger, can be used to track and verify prescription information, payment, dosage taken/used, dosage remaining/unused, monitor chain of custody and associated authorization, etc.

Distributed Ledger

A blockchain is a list of records or blocks that are linked and grow to track a history of transactions and/or other evolution of information. The blocks in the blockchain provide a history of the transaction and/or other information state. The blockchain can be public (e.g., readable by anyone) or private (e.g., encrypted to be read only by those with a key). A blockchain and/or other distributed ledger technology can be used as a digital tool to manage physical assets that are traded between many entities. Blockchain and other distributed ledgers provide technological advantages including transparency and traceability of tracking assets and enablement of transactions, for example.

Blockchain technology is a distributed computing mechanism designed to provide a degree of fairness such that one entity is not advantaged while another entity is disadvantaged. A blockchain is a distributed, public ledger of transactions (e.g., financial transactions, data transactions, etc.) in which the transactions are recorded publicly and chronologically and can be verified by participants without a central authority. Blockchain applies cryptographic algorithms to a shared or distributed database to allow any user to read the database, add to the database, and to help ensure no single user can control what is written to the distributed database. Any blockchain user can view all transactions with respect to the distributed database. Blockchain technology provides disintermediation to reduce intermediaries in communication between data producers and data consumers, for example. That is, rather than engaging a middleman to facilitate a transaction, two entities (e.g., a data consumer and a data supplier) can connect and engage in a transaction directly. Other entities can see the transaction, so the blockchain serves as a distributed consensus engine for the entities to verify and/or otherwise agree to the existence of the transaction.

Figure 2:
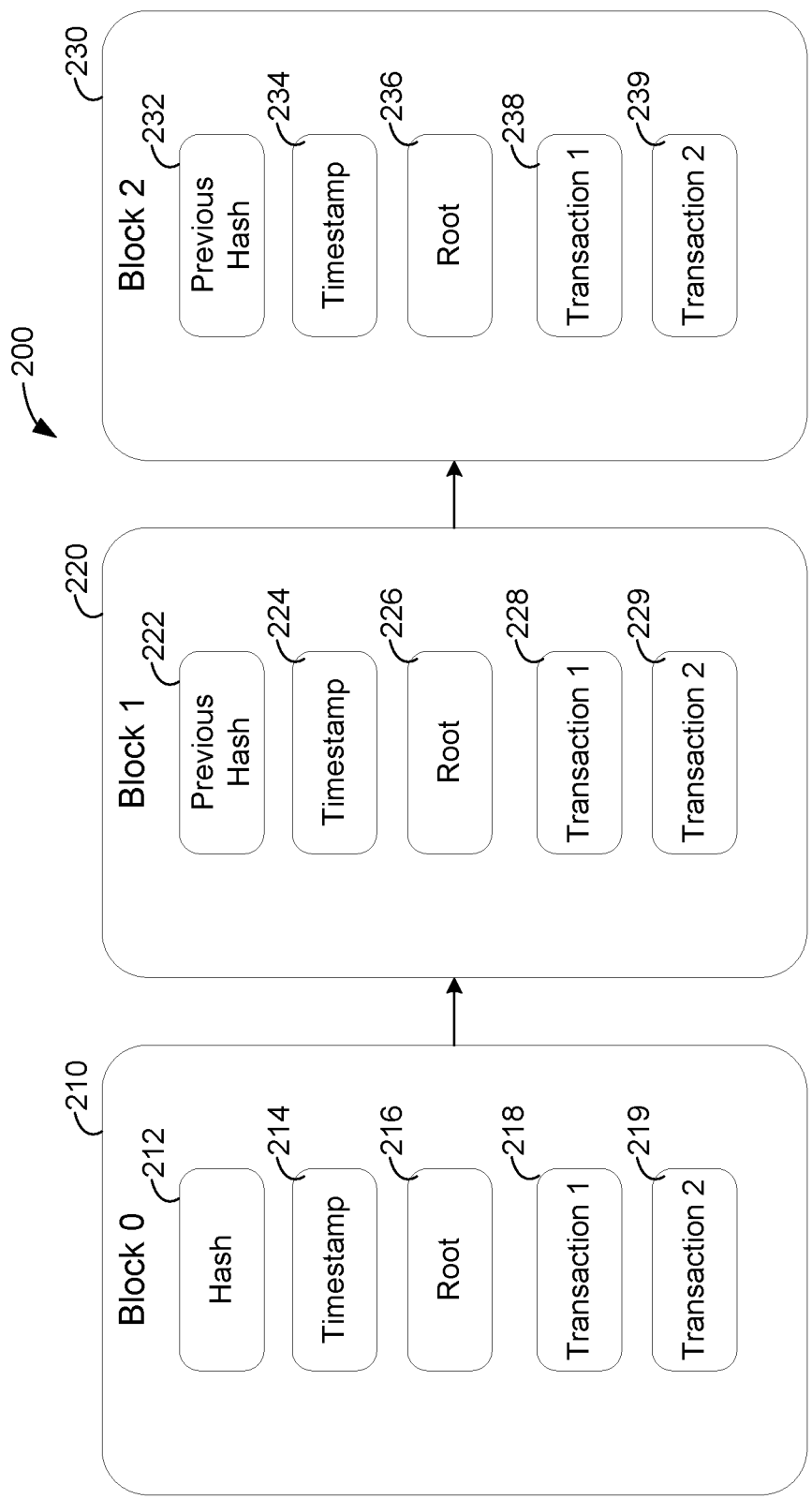
FIG. 2 illustrates an example distributed ledger.

FIG. 2 illustrates an example blockchain 200 including a plurality of records or blocks 210, 220, 230. Each record 210, 220, 230 includes a hash value 212, 222, 232 (e.g., a hash value or other address of a previous block in the chain 200), a timestamp 214, 224, 234 of the record 210, 220, 230, and an address of a root 216, 226, 236 of the blockchain 200. Further, each record 210, 220, 230 includes transactions 218-219, 228-229, 238-239 associated with the respective record 210, 220, 230. Thus, the blockchain 200 is a chain of time-stamped, cryptographically secured, immutable blocks of consensus-validated data. The chain or ledger 200 exists with multiple users, in multiple places, as a series of synchronized copies, for example.

In certain examples, transactions 218-219, 228-229, 238-239 (e.g., prescription, approval, usage, payment, remainder, etc.) can be captured in the blocks 210-230 of the blockchain 200. In certain examples, the first block 210 has a header with a hash 212 of the data stored in the block 210. The second block 220 has a header with a hash 222 of the first block's 210 header information as well as a hash of the second block's 220 data. The third block 230 has a header with a hash 232 of the second block's 220 header information as well as a hash of the third block's 230 data, for example. Thus, the blocks 210-230 are connected and/or otherwise associated with each other and can be used, such as via the hash 212-232, to validate each other, verify associated transactions 218-219, 228-229, 238-239, confirm usage, trigger reordering and/or other instruction, etc.

II. Example Prescription Management Systems and Associated Methods

Figure 3:
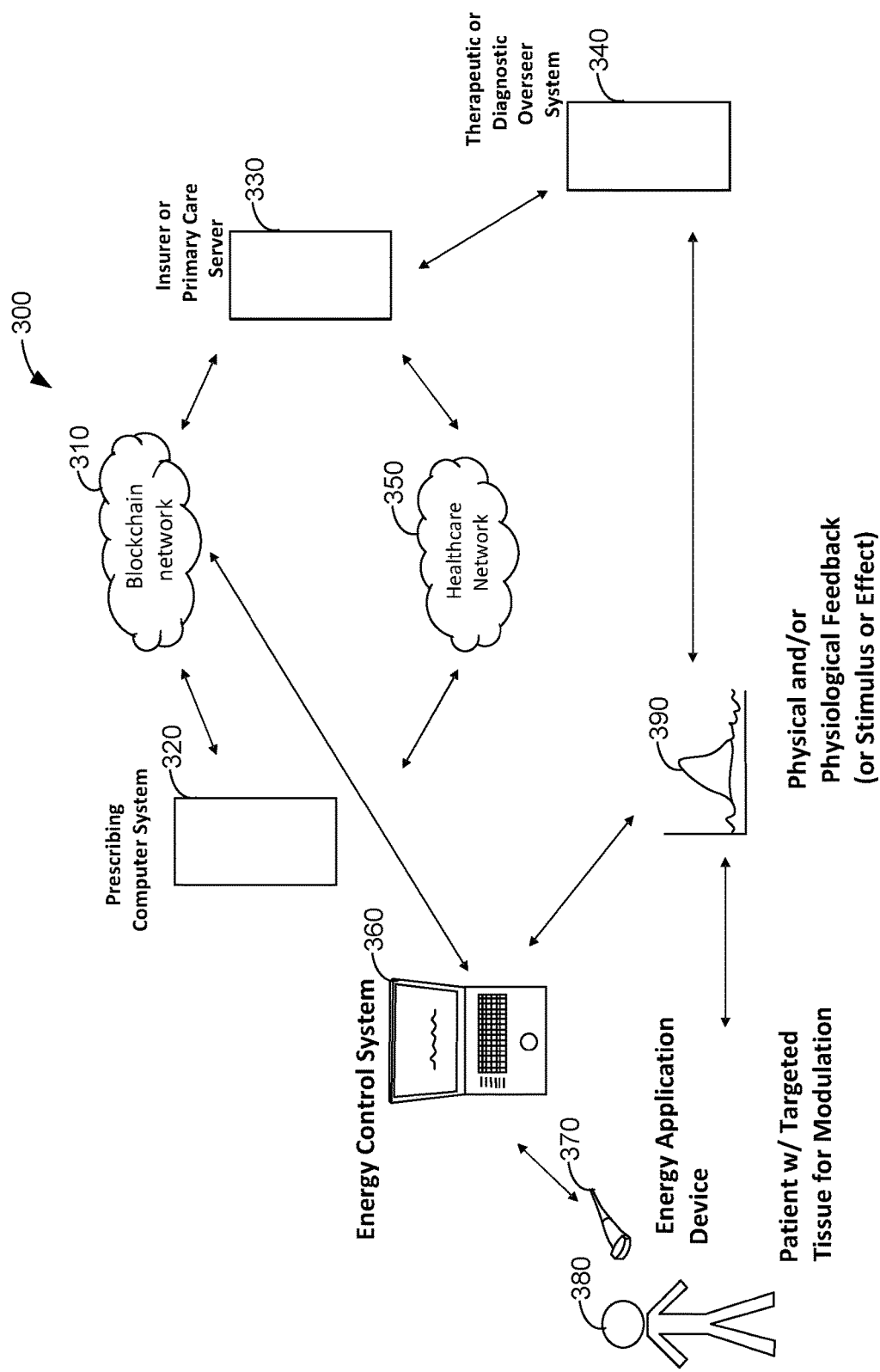
FIG. 3 depicts an example prescription and device management system to guarantee and record dosage and/or other prescription information.

FIG. 3 depicts an example prescription and device management system 300 to guarantee and record dosage and/or other prescription information. As shown in the example of FIG. 3, a blockchain and/or other distributed ledge network 310 is in communication (e.g., wired and/or wireless communication) with a prescribing computer system 320 and an insurer/primary care server 330. The blockchain network 310 records transactions between the prescribing computer system 320 and the care server 330, for example. The insurer and/or primary care server 330 is in communication (e.g., wired and/or wireless communication) with a therapeutic or diagnostic overseer system 340. The insurer/primary care server 330 and the prescribing computer system 320 are also in communication (e.g., wired and/or wireless communication) with a healthcare network 350. The healthcare network 350 provides a conduit for instructions, configuration, reporting, etc. An energy control system 360 can also communicate with the prescribing computer system 320 and the insurer/primary care server 330 via the blockchain network 310 and the healthcare network 350.

Thus, instructions for a prescription, device configuration, other transaction, etc., can be transmitted between the prescribing computer system 320, the insurer/primary care server 330, and/or the energy control system 360 via the healthcare network 350, and a record of the transaction(s) is generated via the blockchain network 310 in which both the prescribing computer system 320, the insurer/primary care server 330, and/or the energy control system 360 maintain a copy of the record. Since both the prescribing computer system 320 and the insurer/primary care server 330 have a copy of the distributed ledger, each system 320, 330 can verify a block added purporting to correspond to a transaction between the computers 320, 330, 360. If a transaction is not verified (e.g., using a hash function, by comparison to another record, etc.), then the block is removed from the blockchain, for example.

The energy control system 360 works with an energy application device 370 (e.g., a transducer probe, etc.) to apply energy to treat a patient 380. For example, the energy control system 360 outputs a modulation stimulus (e.g., neuromodulation, ultrasound, etc.) to a targeted area of patient tissue based on a prescription from the prescribing computer system 320 verified by the insurer/primary care server 330. Instructions can be transmitted via the healthcare network 350, and record(s) of the prescribing, dosage, and configuration of the energy control system 360 and its energy application device 370 can be maintained and verified by comparison via the blockchain network 310. A physical and/or physiological feedback, stimulus, and/or effect 390 can be captured by the energy control system 360 after application by the energy application device 370 and provided to the therapeutic/diagnostic overseer system 340, for example. Alternatively or in addition, the therapeutic/diagnostic overseer system 340 can provide stimulus configuration information 390 to the energy control system 360 for delivery via the energy application device 370, for example.

In some neuromodulation examples, direct, focused modulation of targeted regions of interest is provided to cause targeted physiological outcomes as a result of the modulation. The targeted region or regions of interest can include any tissue or structure in the body having axon terminals forming synapses with non-neuronal cells or fluids. For example, the region of interest can be in an organ or structure, such as a spleen, liver, pancreas, or gastrointestinal tissue, etc. In another example, the regions of interest may be in a lymph system tissue. Neuromodulation of regions of interest permits a local, limited, and nonablative application of energy to only the targeted regions of interest and without the energy being applied outside of the regions of interest. Energy application can trigger downstream effects outside of the targeted regions of interest such as in the same organ, tissue or structure containing the region of interest or in other organs and structures that do not contain the targeted region of interest. In certain examples, downstream effects can be induced in areas of a hypothalamus. The energy application can also induce effects along the targeted nerve upstream from the site of the energy application. In certain examples, effects outside of the targeted region(s) of interest can be achieved without direct energy application to areas outside of the region(s) of interest where the downstream effects or upstream effects are induced. Accordingly, local energy application can be used to realize or achieve systemic effects which may include local effects, downstream effects and/or upstream effects.

Further, the stimulus can facilitate bi-directional control of complex physiological processes. For example, to avoid excess activation of one pathway and excess change of physiological outcomes as a result of energy application at a particular region of interest, energy can be applied to a different region of interest that is associated with a competing pathway or a deactivation pathway to induce change of physiological outcomes in an opposite direction and to maintain a dynamic equilibrium of the physiological outcomes for achieving desired physiological outcomes. In an example, to achieve a desired circulating glucose concentration or concentration range in a hyperglycemic subject, energy is applied to a region of interest that causes a decrease in a circulating glucose concentration. However, to avoid overcorrection of glucose and resulting hypoglycemia, energy can also be applied to a second region of interest that causes an increase in the circulating glucose concentration to maintain a dynamic equilibrium of the circulating glucose concentration and stabilize the circulating glucose concentration to a desired level. For example, if direct energy application to the liver causes a decrease in glucose beyond a clinically acceptable level, then energy can also be applied to the pancreas to increase glucagon production to compensate. Bi-directional stimulation can be provided to a first region of interest in a first organ and a second region of interest in a second organ. In another example, multi-site neuromodulation can be neuromodulation performed on different sites that enhance same pathways. The energy application to the first region of interest and the second region of interest can be simultaneous or at different times (e.g., separated by seconds, minutes, day, or hours, etc.) and can be performed by the same or different energy application device 370, for example.

Certain examples can be used to exert external control on physiological processes of the body to cause targeted physiological outcomes in subjects. Via neuromodulation to the targeted regions of interest, for example, physiological processes can be altered, slowed, halted, or reversed. Certain examples can be applied to subjects to promote dynamic equilibrium or homeostasis of physiological processes, such as glucose regulation, etc. The targeted neuromodulation can function in opposition to ongoing pathogenesis or disease progression to provide treatment and to improve outcomes relative to control (e.g., relative to untreated subjects, etc.). In some examples, the targeted neuromodulation can be preventative and can be initiated prior to certain events. For example, targeted neuromodulation can be used to prevent appetite loss associated with certain medical treatments or conditions and/or can be applied before or during meals to alter the body's response to the meal.

Neuromodulation to the targeted regions of interest can exert a change in physiological processes to interrupt, decrease, or augment one or more physiological pathways in a subject to yield the desired physiological outcome. Further, because the local energy application can result in systemic changes, different physiological pathways can be changed in different ways and at different locations in the body to cause an overall characteristic profile of physiological change in the subject caused by and characteristic of the targeted neuromodulation for a particular subject. While these changes are complex, the present neuromodulation techniques provide one or more measurable targeted physiological outcomes that, for the treated subjects, are the result of the neuromodulation and that may not be achievable without the application of energy to the targeted region/s of interest or other intervention. Further, while other types of intervention (e.g., drug treatment, etc.) may yield a subset of the physiological changes caused by neuromodulation, in certain examples, the profile of the induced physiological changes as a result of the neuromodulation can be unique to the neuromodulation (and its associated modulation parameters) at the targeted region(s) of interest and can differ from patient to patient.

The neuromodulation techniques discussed herein can be used to cause a physiological outcome of a change in concentration (e.g., increased, decreased, etc.) of a molecule of interest and/or a change in characteristics of a molecule of interest. That is, selective modulation of one or more molecules of interest (e.g., a first molecule of interest, a second molecule of interest, etc.) can refer to modulating or influencing a concentration (circulating, tissue) and/or characteristics (covalent modification) of a molecule as a result of energy application to one or more regions of interest (e.g., a first region of interest, a second region of interest, etc.) in one or more tissues (e.g., a first tissue, a second tissue, etc.). Modulation of a molecule of interest can include changes in characteristics of the molecule such as expression, secretion, translocation of proteins and direct activity changes based on ion channel effects either derived from the energy application itself or as a result of molecules directly effecting ion channels. Modulation of a molecule of interest can also refer to maintaining a desired concentration of the molecule, such that expected changes or fluctuations in concentration do not occur as a result of the neuromodulation. Modulation of a molecule of interest can refer to causing changes in molecule characteristics, such as enzyme-mediated covalent modification (changes in phosphorylation, aceylation, ribosylation, etc.). That is, it should be understood that selective modulation of a molecule of interest can refer to molecule concentration and/or molecule characteristics. The molecule of interest can be a biological molecule, such as one or more of carbohydrates (monosaccharaides, polysaccharides), lipids, nucleic acids (DNA, RNA), or proteins. In certain examples, the molecule of interest can be a signaling molecule such as a hormone (an amine hormone, a peptide hormone, a steroid hormone, etc.).

Certain examples described herein record, track, and verify neuromodulation techniques that cause targeted physiological outcomes for the treatment of glucose metabolism and associated disorders. Glucose regulation is complex and involves different local and systemic metabolic pathways. Application of energy to targeted region/s of interest causes characteristic changes in these metabolic pathways to improve glucose regulation. In some examples, modulation at one or more regions of interest can be used to treat disorders including but not limited to, diabetes (e.g., type 1 or type 2 diabetes, etc.), hyperglycemia, sepsis, trauma, infection, physiologic stress, diabetes-associated dementia, obesity, other eating or metabolic disorders, etc. In some examples, neuromodulation can be used to promote weight loss, control appetite, treat cachexia, or increase appetite. In an example, physiologic stress can be medically defined to include a variety of acute medical conditions (e.g., infection, severe injury/trauma, heart attack, bypass, etc.) as well as surgical instances with presentation of hyperglycemia. For example, direct pancreatic stimulation can result in increased appetite, while direct liver stimulation can cause a decrease in NPY, which in turn promotes signals of satiety. The targeted physiological outcome can include tuning circulating (e.g., blood) glucose concentrations in a subject to be within a desired concentration range associated with normal glucose levels and avoiding hyperglycemia or hypoglycemia. Thus, selective modulation of a molecule of interest can be achieved. The tuning can be a result of induced changes in glucoregulatory hormones in the blood or tissue via targeted neuromodulation to cause the desired glucose concentration (e.g., desired glucose end point), for example. Further, glucose regulation can be beneficial for healthy patients without a disease diagnosis, but who are pre-diabetic or who are hoping to maintain a healthy weight, for example.

Using the example system 300, dose recording and reliability/guarantee of dosage information can be facilitated using the blockchain 310 and healthcare 350 networks. The overseer system 340 can verify a stimulus 390 (e.g., a neuromodulation stimulus, ultrasound stimulus, etc.), help the energy control system 360 and energy application device 370 to generate the stimulus 390, and/or process feedback from the stimulus 390, etc., while the prescribing computer system 320 provides instructions for the energy control system 360 to apply the stimulus 390 and the insurer/primary care server 330 verifies coverage and/or payment for the stimulus delivery to the patient 380, for example. Instructions, commands, feedback, reporting, etc., can be exchanged via the healthcare network 350, and the distributed ledger is built, maintained, and verified via the blockchain network 310.

Thus, the healthcare communication infrastructure 300 provides secure management and recording of doses of energy given to a patient for therapeutic purposes, using secure methods to validate the given doses via the distributed ledger of the blockchain network 310. The energy device 370 provides the energy stimulus 390 to the patient's 380 internal/external tissue makes a change to an electronic document and can transmit the change to the blockchain network 310. A dose log chain residing on the network 310 and shared among all the nodes on the network stores dose information. A node on the network 310 can verify a change of dosing or therapeutic output made by other nodes and add a new block to the chain using one-way hashes, for example, making the chain resistant to tampering. If an invalid block is detected, the system can send an auditing alert to the network 310. The audit log can be strongly resistant to tampering, providing reliable evidence for use in auditing patient compliance, therapeutic effectiveness, therapeutic device function, and/or patient/dose record keeping, for example.

Figure 4:
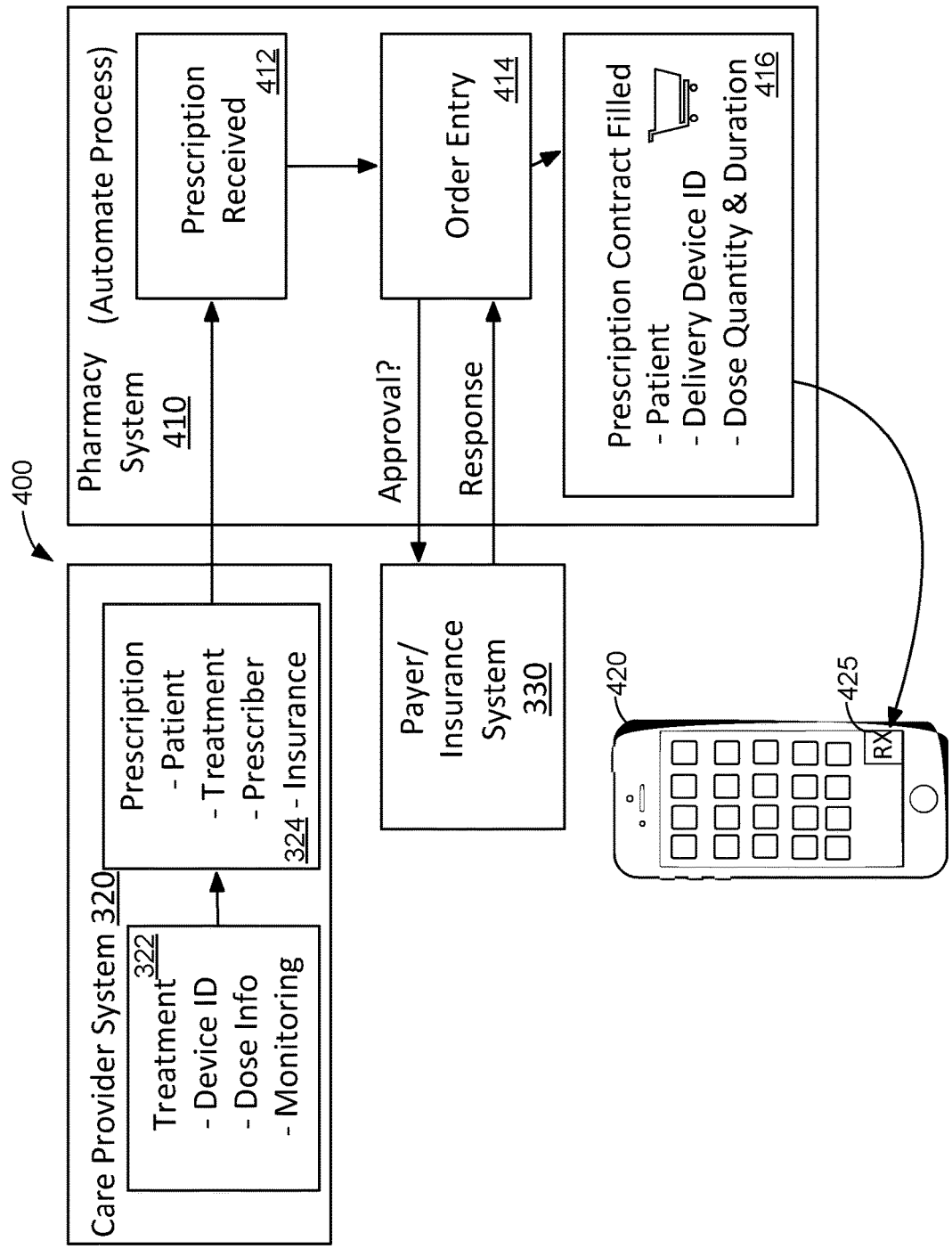
FIG. 4 illustrates an example ecosystem of actors and attributes to deliver prescription and dose to a patient device.

FIG. 4 illustrates an example ecosystem 400 of actors and attributes to deliver prescription and dose to a patient device. As shown in the example of FIG. 4, system actors, such as the care provider system 320, pharmacy system 410, payer/insurance system 330, patient device 420, etc., and associated attributes such as treatment 332, prescription 334, etc., facilitate instantaneous (or substantially instantaneous given communication and processing latency, etc.) prescription and dosing of therapeutic stimuli by automating the delivery of prescribed therapy to the user's device 420. For example, the care provider system 320 includes a data structure defining a treatment 332 including a device identifier, dose information, monitoring protocol, etc., and a data structure defining a prescription 334 including a patient identifier, a treatment identifier, a prescriber identifier, an insurance identifier, etc. The prescription is accessed 412 by the pharmacy system 410 and used to generate an order entry 414 that is approved or denied by the payer/insurance system 330 processing the prescription order in comparison to an insurance policy and/or other coverage. An approved order results in filling the prescription contract 416 including a patient identifier, a delivery device identifier, a dose quantity and duration, etc. The filled prescription contract can be accessed as an electronic prescription contract 425 to the user's computing device 420 (e.g., a cellular phone, a tablet computer, other handheld or mobile computing device, etc.). In certain examples, the user's device 420 can serve as the energy control system 360 to drive/control the energy application device 370 according to the approved prescription 425.

Figure 5:
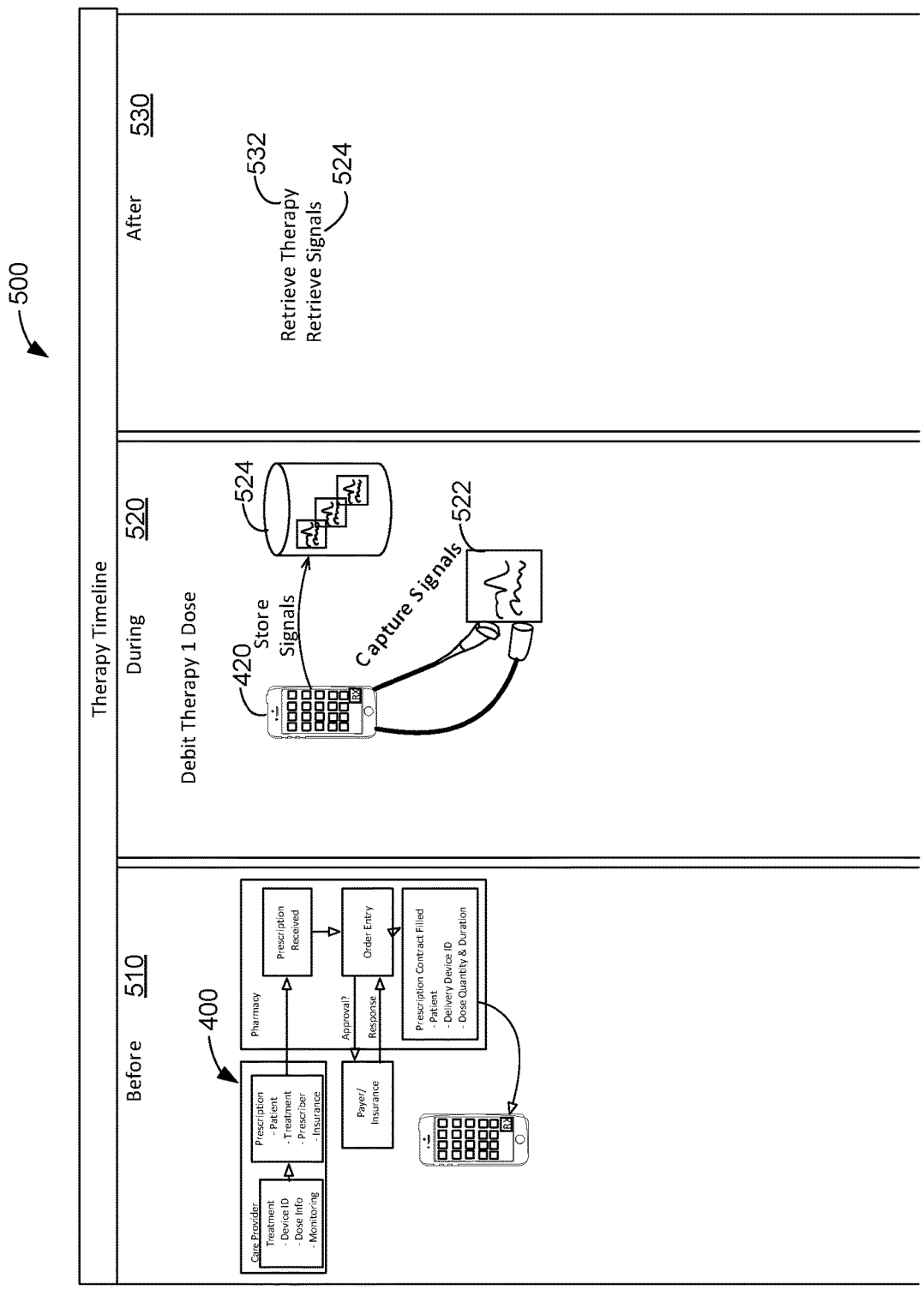
FIG. 5 illustrates an example therapy timeline or workflow for dose prescription, delivery, and auditing.

FIG. 5 illustrates an example therapy timeline or workflow 500 for dose prescription, delivery, and auditing. At block 510, before therapy is applied to a patient, the example system 400 approves the prescription and prepares the user device 420 for therapy via the electronic prescription 425. At block 520, therapy is provided. Therapy can include application of stimulus 390 to the patient 380, and the user device 420 can control the energy application device 370 and/or capture data related to the therapy. For example, the device 420 can capture signals 522 related to the stimulus 390 and can store the captured signals 524 for analysis, further control of the therapy, update of the distributed ledger record, etc. Data to capture can include probe 370 position, inertial measurement unit (IMU) data, imaging data, patient identity, dose information, device identity, biological measure(s) (e.g., blood, electrical, etc.), elastography (e.g., mechanical response of tissue, etc.), local blood flow, etc. At block 530, a post-therapy phase includes retrieving therapy information 532, stored signals 524, etc., for further analysis, device reconfiguration, etc.

Figure 6:
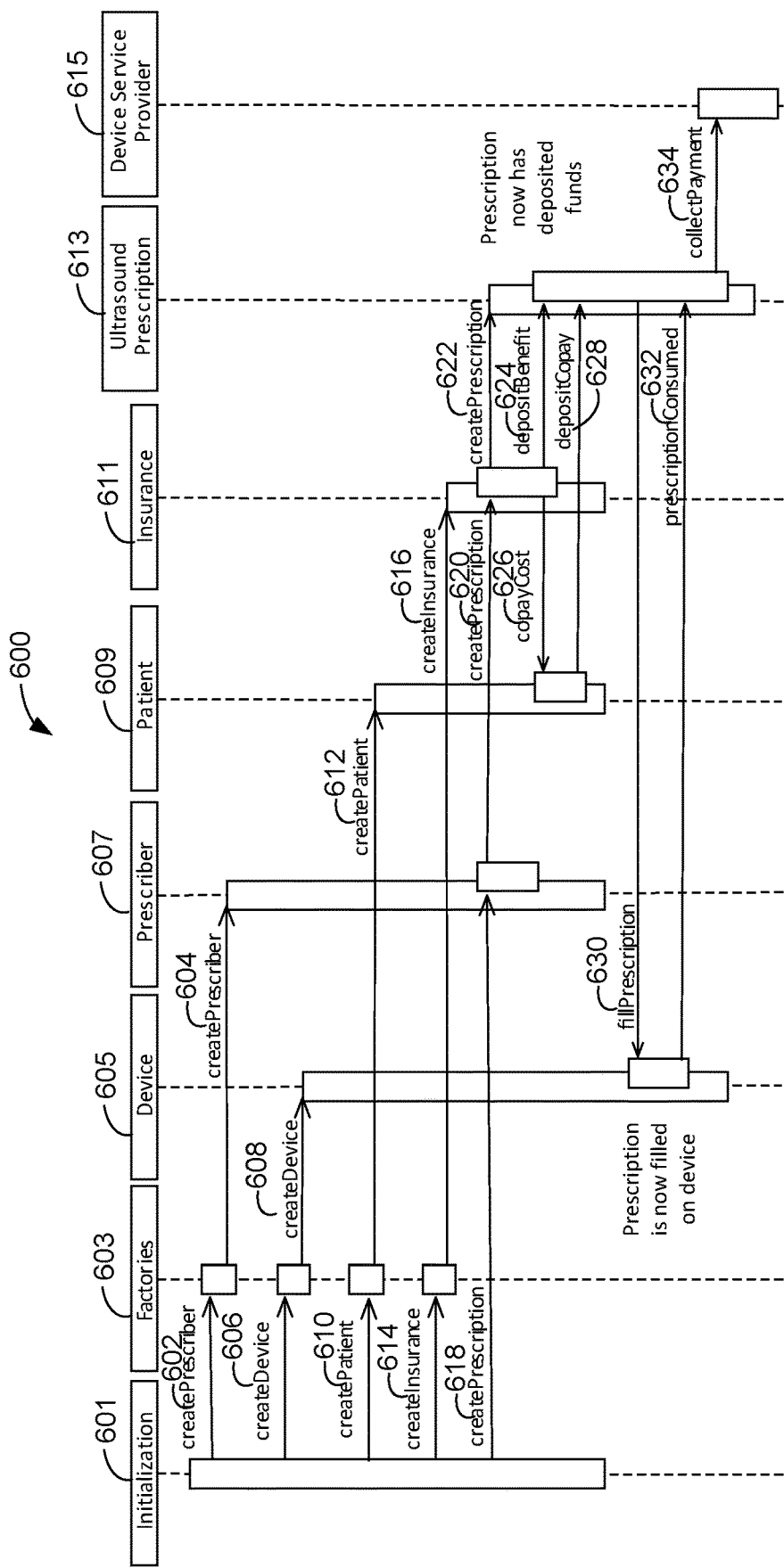
FIG. 6 depicts an example data flow diagram for prescription management involving a plurality of data structure constructs that represent actors in a therapy workflow and characterize those actors to provide executable/actionable instructions to drive prescription management.

FIG. 6 depicts an example data flow diagram 600 for prescription management involving a plurality of data structure constructs that represent actors in a therapy workflow and characterize those actors to provide executable/actionable instructions to drive prescription management including filling, verification, delivery, updating, etc. The executable code constructs driving the example data and instruction flow 600 include initialization 601, factories 603, a device 605, a prescriber 607, a patient 609, insurance 611, an ultrasound prescription 613, and a device service provider 615. Each construct 601-615 and its interaction with other construct(s) 601-615 can generate an update and associated verification in a distributed ledger, for example.

At initialization at 602, an instruction is sent to the factories 603 (e.g., the instruction is sent to a software factory that includes software assets to produce computer software applications and/or other software components, etc.) to create or instantiate the prescriber 607 as a software and/or data construct (e.g., a machine learning and/or other artificial intelligence model, software application, etc.) to create prescriptions and associated software and/or data constructs. At 604, the factories 603 spawn the prescriber 607 (e.g., the software and/or data construct forming the prescriber 607 is coded and/or otherwise formed by the factories 603 and deployed for use/execution, etc.).

The initialization 601 also triggers, at 606, creation of a device software and/or data construct representing the device 605, such as the energy application device 370, to be included in the prescription. At 608, the factories 603 spawn the device construct 605.

The initialization 601 also triggers, at 610, creation of a patient software and/or data construct representing the patient 609, such as the patient 380, to be a target of the prescription. At 612, the factories 603 spawn the patient construct 609.

The initialization 601 also triggers, at 614, creation of an insurance software and/or data construct representing the insurance 611 to be associated with the prescription. At 616, the factories 603 spawn the insurance construct 611.

The initialization 601 also triggers, at 618, creation of a prescription software and/or data construct representing the prescription 613, such as an ultrasound prescription, etc. At 620, the factories 603 spawn the prescription construct 613 for the insurance construct 611. A definition of the prescription provided in the prescription construct 613 is compared to rules, constraints, data associated with the patient construct 609, etc., to create, based on device and patient requires, insurance constraints, etc., the prescription (e.g., the ultrasound prescription 613, etc.) at 622. At 624, a benefit is deposited from the insurance construct 611 to the prescription 613, and, at 626, a copay cost is provided from the insurance construct 611 to the patient construct 609. In addition to the benefit from the insurance construct 611, at 628, the patient construct 609 can trigger deposit of a copay with the prescription 613.

The prescription construct 613 (e.g., the ultrasound prescription, other medical device prescription, other energy prescription, pharmaceutical prescription, etc.) now includes deposited funds from the insurance benefit and patient copay, and, at 630, can fill the prescription at the device 605. For example, the prescription construct 613 can instruct and/or otherwise configure the device construct 605 according to the ultrasound prescription for the energy application device 370 modeled by and/or otherwise associated with the device construct 605. The device 605 can then execute according to the prescription 613, such as instructing/configuring the device 370 to treat the patient 380 according to a certain energy dosage, setting, etc. Thus, at 632, the prescription 613 is consumed (e.g., by the device 370 for the patient 380, etc.). At 634, the device service provider 615 collects payment for consumption of the prescription 613, such as from the funds (e.g., insurance benefit and/or copay, etc.) stored in the prescription construct 613.

For example, each construct 601-615 and/or its associated transactions 602-634 can be modeled as a record 210-230 in a distributed ledger 200. Each creation/initialization transaction 602-622 to create the device 605, prescriber 607, patient 609, insurance 611, prescription 613, etc., can be accompanied by a record 210-230 in the ledger 200. Each actor such as the prescribing computer system 320, insure/primary care server 330, overseer system 340, energy control system 360, etc., can maintain a copy of the ledger 200 to verify accuracy of its records 210-230 and changes to those records 210-230 (e.g., via hashing, proof of work, other matching/verification, etc.). Update of the prescription 613 with added funds and/or deducted payment 624-628, 634 can be an update to a record 210-230 representing the prescription 613, patient 609, insurance 611, etc., and/or a new record 210-230 added to the distributed ledger 200 representing the transaction 624-628, 634, for example. Filling and consumption of the prescription 630-632 can also be conveyed as an update to a record 210-230 representing the prescription 613 and/or a new record 210-230 added to the distributed ledger 200 representing the transaction 630-632, for example.

While the example of FIG. 6 sets forth one data flow for prescription management, other data flows can be implemented. For example, another entity, such as insurance 611, can create prescriber 607 and patient 609, device manufacturing can create the device 605, etc.

Figure 7:
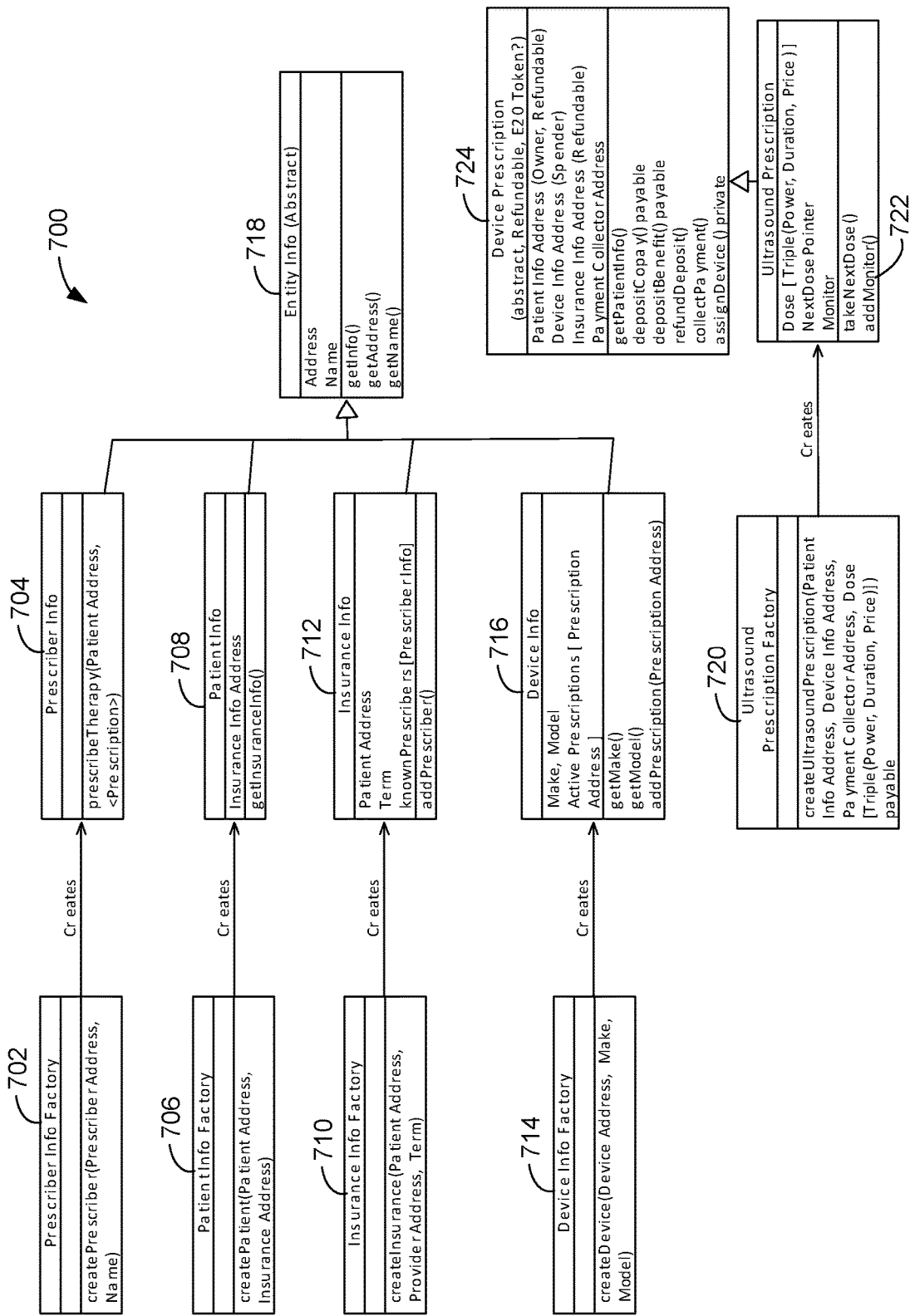
FIG. 7 illustrates a combination of example data constructs, data structures, class definitions, software executable constructs, etc., driving the data and instruction flow of the example of FIG. 6.

FIG. 7 illustrates a combination 700 of example data constructs, data structures, class definitions, software executable constructs, etc., 702-724 driving the data and instruction flow 600 of the example of FIG. 6. FIG. 7 illustrates logical data models to provide class diagrams showing data and functionality definitions. As shown in the example of FIG. 7, a prescriber information factory 702 includes a function to create a prescriber information construct 607 including a prescriber name, prescriber address, etc. The prescriber information factory function 120 creates a prescriber construct 704 including a prescribe function such as a prescribe therapy function leveraging a patient address and prescription information to generate prescription information.

Additionally, a patient information factory 706 defines a patient creation function using patient address, insurance address, etc., to create a patient information construct 708 including insurance information for the patient and a function to provide associated insurance information. Further, an insurance information factory 710 defines an insurance creation function using patient address, provider address, term, etc., to create an insurance information construct 712 including patient address, insurance term(s), and prescriber information such as known prescriber(s), ability to add prescriber(s), etc. A device information factory 714 defines a device creation function using device address, make, model, etc., to create a device information construct 712 including make, model, active prescription(s) (e.g., with prescription address, etc.) and associated functions to get make, get model, add prescription, etc.

An entity 718 can be formed from the prescriber model 704, the patient model 708, the insurance model 712, and the device model 716. The entity model or construct 718 can include name information, address information, etc., and functions including an information retrieval function (e.g., getInfo( ) etc.), an address retrieval function (e.g., getAddress( ) etc.), a name retrieval function (e.g., getName( ) etc.), etc.

As shown in the example of FIG. 7, an ultrasound prescription factory 720 provides a function to create an ultrasound prescription based on patient information construct address, device information construct address, payment collector address, dose (e.g., a triple of power, duration, price, etc.), payable, etc. The ultrasound prescription factory 720 creates an ultrasound prescription 722 including dose (e.g., a triple of power, duration, price, etc.), net dose pointer, monitor, etc., and associated function to take next dose, add monitor, etc. The example ultrasound prescription 722 can be provided to a device prescription 724 including patient information address (e.g., including owner, refundable indicator, etc.), device information address (e.g., including a spender identifier, etc.), insurance information address (e.g., including a refundable indicator, etc.), payment collector address, etc. The device prescription 724 can also include functions such as get patient information, deposit copay payable, deposit benefit payable, refund deposit, collect payment, assign device, etc.

Using the entity 718, the ultrasound prescription 722, and the device prescription 724, data can be stored and verified for energy delivery to a patient. For example, the entity and prescription information 718, 722, 724 can include and/or be used to verify a person that is receiving doses. For example, the construct(s) 718, 722, 724 can be formatted as and/or be associated with records 210-230 in a distributed ledger 200 to form a digital pharmacy log of patient and associated doses (e.g., for each dose). Confirmation of patient and dosage can be determined using biometric data such as images taken of the patient, device, material, etc., by the patient's smartphone and/or other electronic device 420, the dosing machine (e.g., the energy device 370, etc.), etc. A number of doses taken by a patient can be verified (e.g., so as to not allow overdosing or addiction to develop, etc.) based on image data, patient sample, other biometric analysis, etc., and stored as part of the prescription and/or entity construct 718, 722, 724, as a corresponding record or records 210-230 in the blockchain 200, etc.

For example, image recognition of the patient's internal and/or external tissue can be used to verify dose on the patient, location, intensity, etc. A tissue and/or other physiological response can be processed to verify amplitude or dose of energy applied according to the ultrasound prescription 722, for example. Feedback from internal and/or external sensors can be used to measure energy being applied according to the device prescription 724 and verified according to the ultrasound prescription 722, for example. Alternatively or in addition, other features, such as changes in blood flow and/or other physiological response, can be used as verification of dosing via the constructs 718, 722, 724 and associated distributed ledger.

For example, records 210-230 of the ledger 200 can be used to store and verify compliance data through proof of work and comparison across devices 320-360, 420, etc., maintaining copies of the distributed ledger 200. Comparison of copies of ledger records 210-230 can be used to verify accuracy of measured data and compliance with device configuration, prescription information, patient status, treatment protocol, etc.

Figure 8:
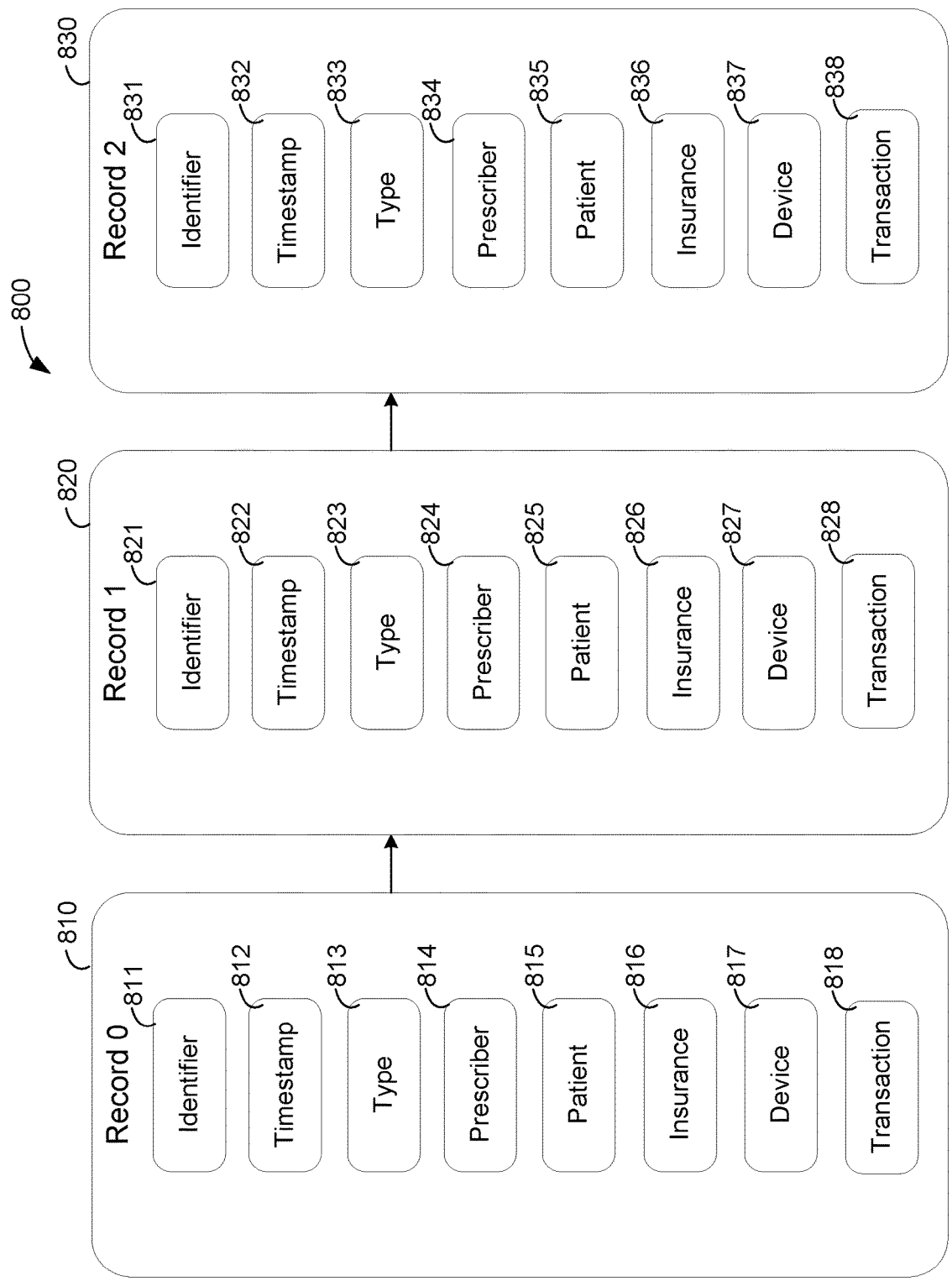
FIGS. 8-9 show example distributed prescription ledgers.

For example, a distributed prescription ledger 800, such as shown in the example of FIG. 8, can include a plurality of records 810-820 characterizing a patient, a device, insurance coverage, associated prescription information, and transactions involving the patient, device, insurance coverage, prescription delivery and renewal, etc. The example ledger 800 is similar to the example blockchain 200 and includes records 810, 820, 830 corresponding to data constructs, software code, and transactions involving a patient, an associated therapy device, the patient's insurance coverage and finances, prescription formation, prescription delivery, prescription renewal, etc.

As shown in the example ledger 800 of FIG. 8, a record 810 is created when a patient 609, 708, 718 is instantiated in the system, when a device 605, 716, such as the energy application device 370, a smart phone and/or other portable computing device 420, etc., is configured for use, when a prescription construct 324, 613, 722, 724 is instantiated, when funding is provided for the prescription, when the prescription is administered, etc. Additional record 820, 830 are created to reflect new transactions and/or other updates/adjustments to the patient, device, insurance, prescription, etc. The example records 810-830 include an identifier 811, 821, 831 associated with the record 810, 820, 380, a timestamp 812, 822, 832 corresponding to the creation and/or update of the record 810-830, a type 813, 823, 833 of the record 810-830 (e.g., a patient record, a device record, an insurer record, a prescription record, an entity record, a dosage record, etc.). The example record 810-830 also includes prescriber information 814, 824, 834, patient information 815, 825, 835, insurance information 816, 826, 836, device information 817, 827, 838, transaction information 818, 828, 838, etc. Using the type 813-833, prescriber 814-834, patient 815-835, insurance 816-836, device 817-837, transaction 818-838, etc., a representation of an entity (e.g., the entity construct 718, etc.) can be formed, for example. The entity record 810 can be updated such as by modifying the record 810 with the transaction 818 and/or adding a subsequent record 820, 830 to the distributed ledger 800 indicating a new transaction 828, 838 to track progress and/or other change in patient therapy, insurance coverage/payment information, device configuration/usage, etc.

Multiple systems 320-360, 420, etc., can maintain copies of the records 810-830 of the distributed ledger 800 to verify record 810-820 content, transaction 818-838, etc. An altered, erroneous, or fraudulent record 810-830 can be identified and repaired, replaced, etc., using another copy of the distributed ledger 800, for example. For example, each system maintaining a copy of the ledger 800 can verify items in the record 810-830, compute a hash of record 810-830 information, solve a proof of work function with respect to the applicable record 81-830, etc.

Figure 9:
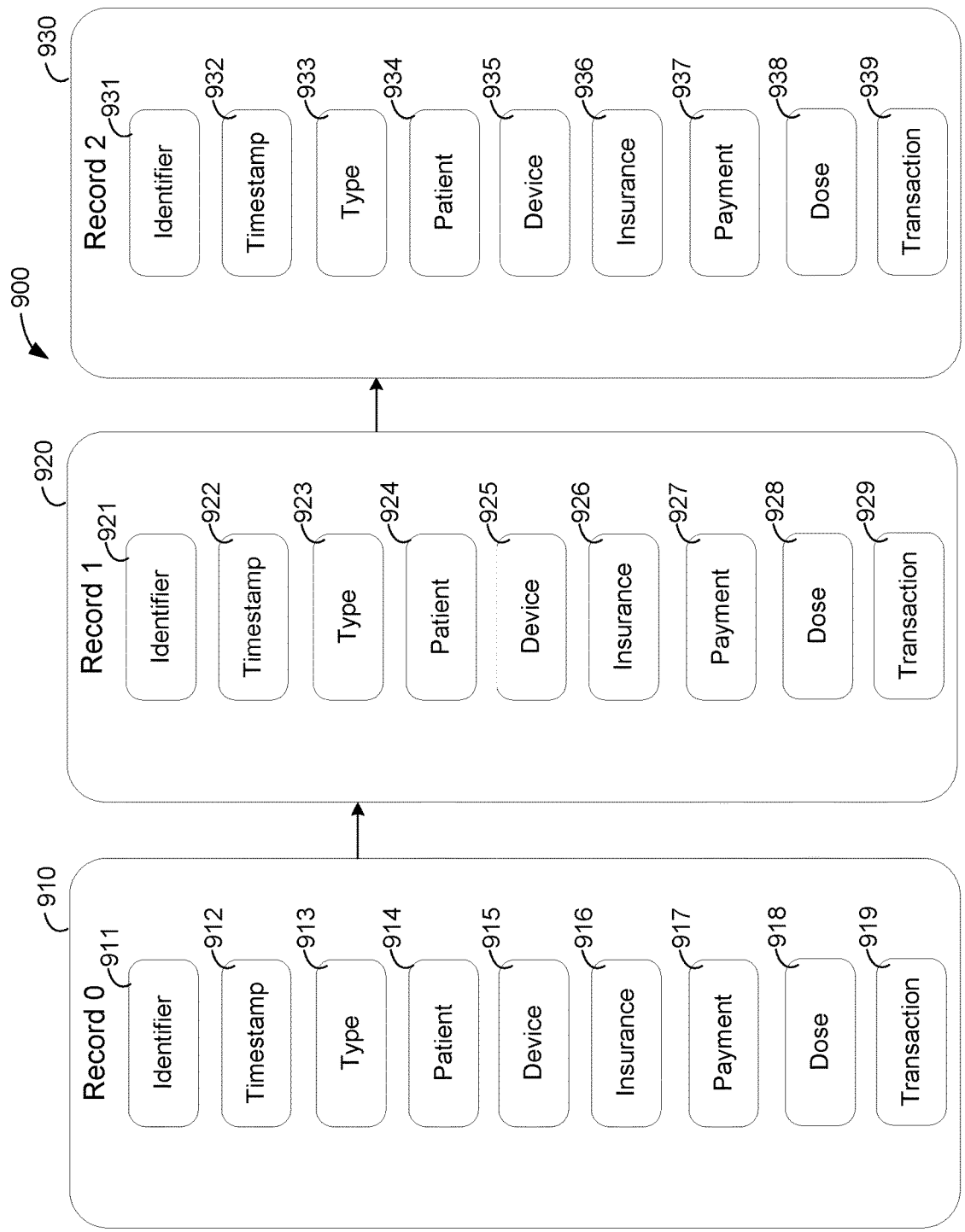

FIG. 9 illustrates another example distributed ledger 900 providing prescription management for a patient. In the example of FIG. 9, records 910-930 identify, monitor, and update a prescription for a device to be applied to a patient. The records 910-930 include an identifier 911, 921, 931, such as a number unique to the ledger 900 identifying the record, a hash of the previous record's identifier, an identifier associated with the patient, etc. The records 910-930 include a timestamp 912, 922, 932 associated with creation and/or update of the record 910-390. The records 910-930 include a type 913, 923, 933 to identify whether the record 910-930 is a new prescription, an update or change in the prescription, a transaction or contract involving the prescription, etc. The records 910-930 include a patient identifier 914, 924, 934, a device identifier 915, 925, 935, an insurance identifier 916, 926, 936, a payment indicator 917, 927, 937, a dose counter 918, 928, 938, a transaction identifier 919, 929, 939, etc.

Using the distributed ledger 900 of records 910-930, patient compliance data can be stored. For example, the patient 914-934, dose 918-938, and transaction 919-939 can be compared across records 910-930 to determine whether the patient is following a "dose" regimen closely or not. The compliance can be compared across patients to determine which patient is following the dose regimen most closely, for example. Dose 918-938, device 915-935, patient 914-934, type 913-933, insurance 916-936, payment 917-937, and transaction 919-939 information can be used to store doctor prescription data and can be compared across ledgers 900 over time to determine which doctors are prescribing most effectively, for example.

In certain examples, transaction data 919-939 can be compared to dose information 918-938 to determine and store a physiological effect of a given dose on the patient 914-934. In certain examples, transaction data 919-939, dose information 918-938, device data 915-935, etc., can be compared to determine device performance in providing the dose and store, track, etc., hardware and/or therapy effectiveness. In certain examples, record 910-930 information enables changing of the prescription based on effectiveness determined by physiological feedback. Thus, dynamic dosing data can be stored in a field 918-938 of the record 910-930.

The records 910-930 of the distributed ledger 900 can be used to handle transactions involving patient treatment through administration of an energy dose according to a prescription, for example. Depending on where the therapeutic dose information is being sent and stored, additional transaction/dosing verification can be provided, such as using image recognition (e.g., of the patient's internal/external tissue) to verify dose on patient, location, etc. For example, tissue and/or physiological response information can be used to verify amplitude and/or dose of the energy applied by the device to the patient. Feedback from internal and/or external sensors that measure the energy being applied can be processed for verification of treatment, for example. Other features, such as changes in blood flow and/or other physiological response, can be tracked by the records 910-930 and used as verification of dosing for example. In certain examples, measures can be used in a consensus algorithm (e.g., personal image recognition, etc.) to verify patient and dosage. The therapeutic hardware can also be tied to another device, such as a cellular phone, etc., to use global position and/or other biometric data to tie a person to the device and verify dosing via transactions 919-939 associated with the records 910-930 in the ledger 900, for example. The ledger 900 can be internal (e.g., for use by a therapeutic company to evaluate usage of its device/system, etc.) and/or external (e.g., the therapeutic company can provide dosing data to other healthcare players, such as insurance companies, etc., to allow value to be derived from dosing information, for example. For example, value derived from dosing data can include different patient insurance premiums based on compliance to a prescribed therapeutic regimen, etc. Value can include different insurance payouts for hospital systems that perform better at diagnosing correct energy application and/or dosing regimen, for example. These actions 919-939 can be added as records 910-930 and/or used to adjust existing records 910-930 of a blockchain or other distributed ledger 900, for example. Participants in the distributed ledger 900 can include a patient, primary healthcare provider(s), therapy provider(s), hospitals and/or healthcare systems, diagnostic and/or therapeutic equipment providers, insurers, insurance claim administrator/investigators, government/guiding agencies, consumer companies that may impact patient health through provision of related or non-related products, and/or other players within healthcare, for example.

Figure 10:
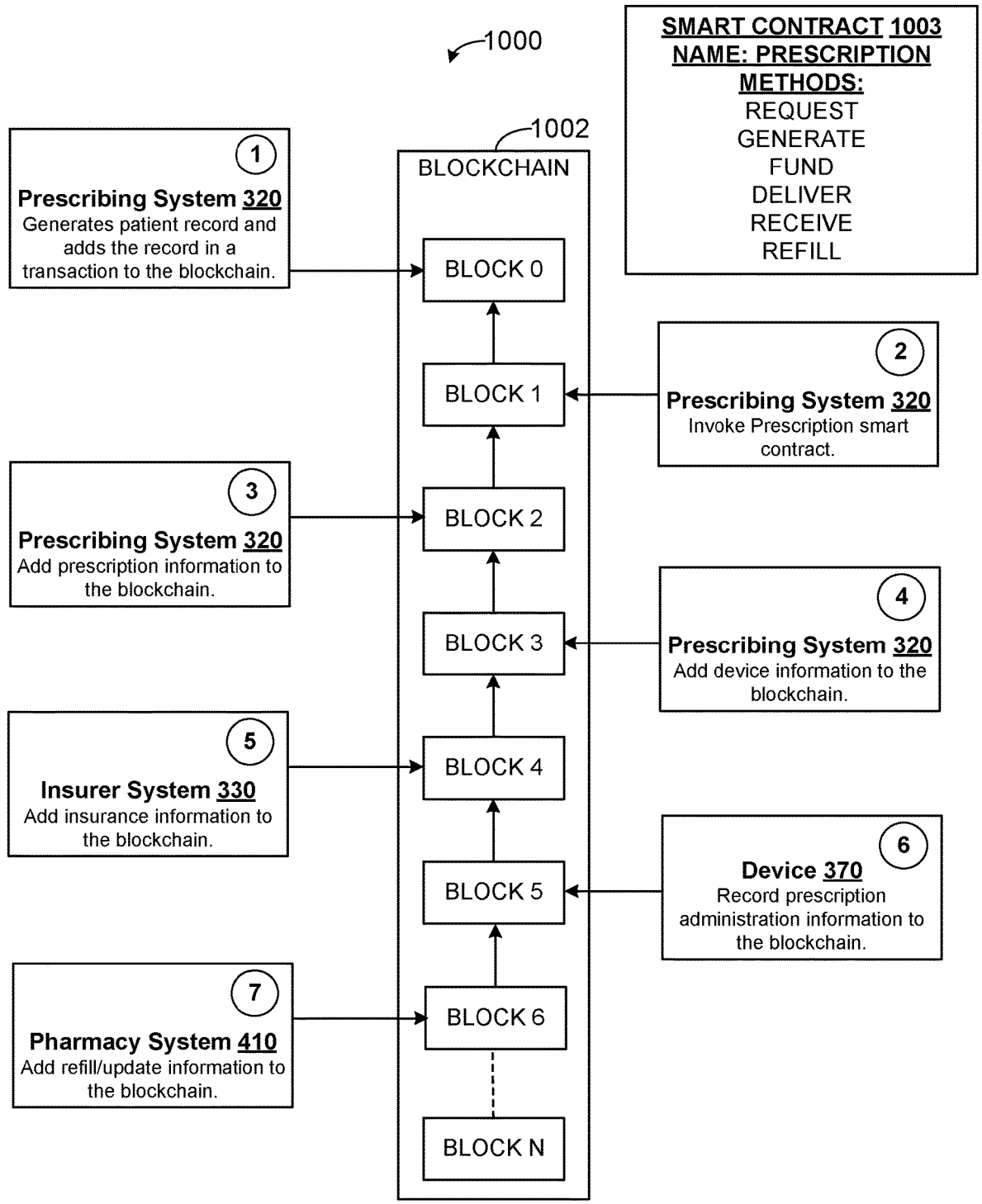
FIG. 10 shows an example transaction flow for an example prescription blockchain.

FIG. 10 shows an example transaction flow 1000 for an example prescription blockchain 1002 (e.g., implementing the example distributed ledger 800, 900 of FIGS. 8 and/or 9). As shown in the example of FIG. 10, at 1, the prescribing system 320 creates a record, which forms Block 0 of the blockchain 1002 and which defines a patient (e.g., the patient construct 609, etc.). At 2, the prescribing system 320 invokes a prescription smart contract 1003. The invocation of the smart contract 1003 is stored as a transaction in Block 1 of the blockchain 1002. At 3, the prescribing system 320 adds prescription 613 information as Block 2 of the blockchain 1002. At 4, the prescribing system 320 adds device 605 information at Block 3 of the blockchain 1002. The device 605 transaction can also include filling of the prescription with the pharmacy/prescription system 410, for example. At 5, the insurer system 330 adds insurance information such as insurance coverage, patient copay, etc., at Block 4 of the blockchain 1002. At 6, the device 370 (e.g., with control system 360, etc.), 605 administers the prescription to the patient, which is recorded as a transaction in Block 5 of the blockchain 1002. At 7, the prescription can be refilled and/or otherwise updated by the pharmacy system 410, which is stored as a transaction at Block 6 of the blockchain 1002. The blockchain 1002 can continued to be updated with additional transactions at Block N, for example.

Figure 11:
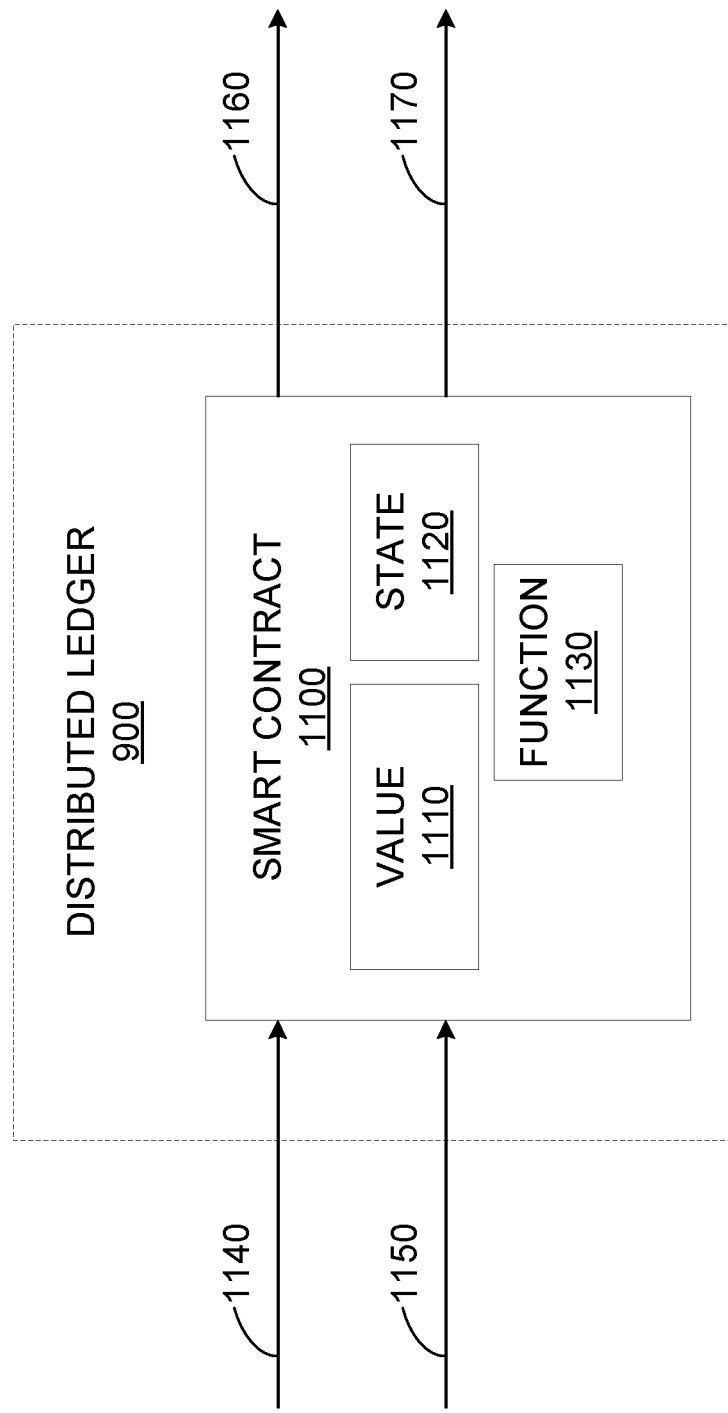
FIG. 11 illustrates an example smart contract for a prescription to deliver energy therapy to a patient that can be tracked via the distributed ledger.

FIG. 11 illustrates an example smart contract 1100 for a prescription to deliver energy therapy to a patient that can be tracked via the distributed ledger 800, 900, for example. The example smart contract 1100 can be stored as a record 810-830, 910-930 in the ledger 800, 900, for example. As shown in the example of FIG. 11, the contract 1100 includes a value 1110 (e.g., a quantity of material, a cost, a timing, etc.) and a state 1120 (e.g., available, completed, executed, in execution, delivered, material remaining, etc.). In certain examples, the contract 1100 can apply to a plurality of patients who are all subject to the same contract terms. Additionally, in certain examples, a current state of the contract can be derived from the value 1110 without storing the state 1120 explicitly. The contract 1100 can also include one or more functions 1130 executable with respect to the contract 1100. Thus, the contract 100 can specify its terms 1110 and a status 1120 of the execution of those terms using one or more functions 1130, for example. For example, such as shown in the example Prescription contract 1003 of FIG. 10, functions 1130 can include request, generate, fund, deliver, receive, refill, update, etc. The contract record 1100 can receive transaction information 1140 and event information 1150 and also provide transaction information 1160 and event information 1170 to another record 810-830, 910-930 in the ledger 800, 900 and/or system, etc.

For example, a transaction 1140 can provide value 1110 to the contract 1100 such as through a quantity of energy to be associated with a prescription and/or other term/condition to the contract 1100. An event 1150 can impact a state 1120 of the contract 1100 such as a time of administering the prescription, an identification of associated device, etc. As the prescription is funded, paid, administered, refilled, etc., transaction information 1160 and event information 1170 can be propagated to another record 810-830, 910-930 as a transaction the ledger 800, 900, for example. Thus, the smart contract 1100 can be used to track transactions involving electronic prescriptions for energy delivery, pharmaceutical, treatment, etc.

The smart contract 1100 can be implemented as computer program code that can be executed to enable/facilitate performance of the contract/agreement between parties (e.g., between a hospital or clinician, a pharmacy, and/or an insurance company, etc.) using the ledger 800. 900. Conditions and/or updates to the contract 1100 can be implemented as processor-executable instructions executed by a processor such as the prescribing computer system 320, the insurer/primary care server 330, the overseer system 340, the energy control system 360, the mobile computing device 420, and/or another processor to implement and/or track execution of the contract 1100. Terms of the contract 1100 can be coded as logic statements governing conditions and results of the contract 1100 and associated material. The contract 1100 can be fully automated to execute on its own with respect to the distributed ledger 800, 900 and/or can be executable by a processor/device (e.g., the prescribing computer system 320, the insurer/primary care server 330, the overseer system 340, the energy control system 360, the mobile computing device 420, and/or another processor, etc.), to fulfill the contract 1100, for example. Thus, the contract 1100 can be formulated entirely in executable code and/or can include additional elements to be interpreted by a processor, for example. The contract 1100 can be executed within the ledger 800, 900 (e.g., code forming the contract 1100 is coded into blocks of the blockchain and/or other distributed ledger 800, 900, etc.) and/or executed outside the ledger 800, 900 and provides information (e.g., new and/or updated records 310-330, etc.) back to the ledger 300, for example. In certain examples, anyone can add a contract 500 and/or make changes to records 310-330 in the ledger 300. In other examples, access to the ledger 300 and associated records 310-330, contracts 500, etc., is restricted such as based on processor authorization (e.g., authorized nodes), user authorization, etc.

Figure 12:
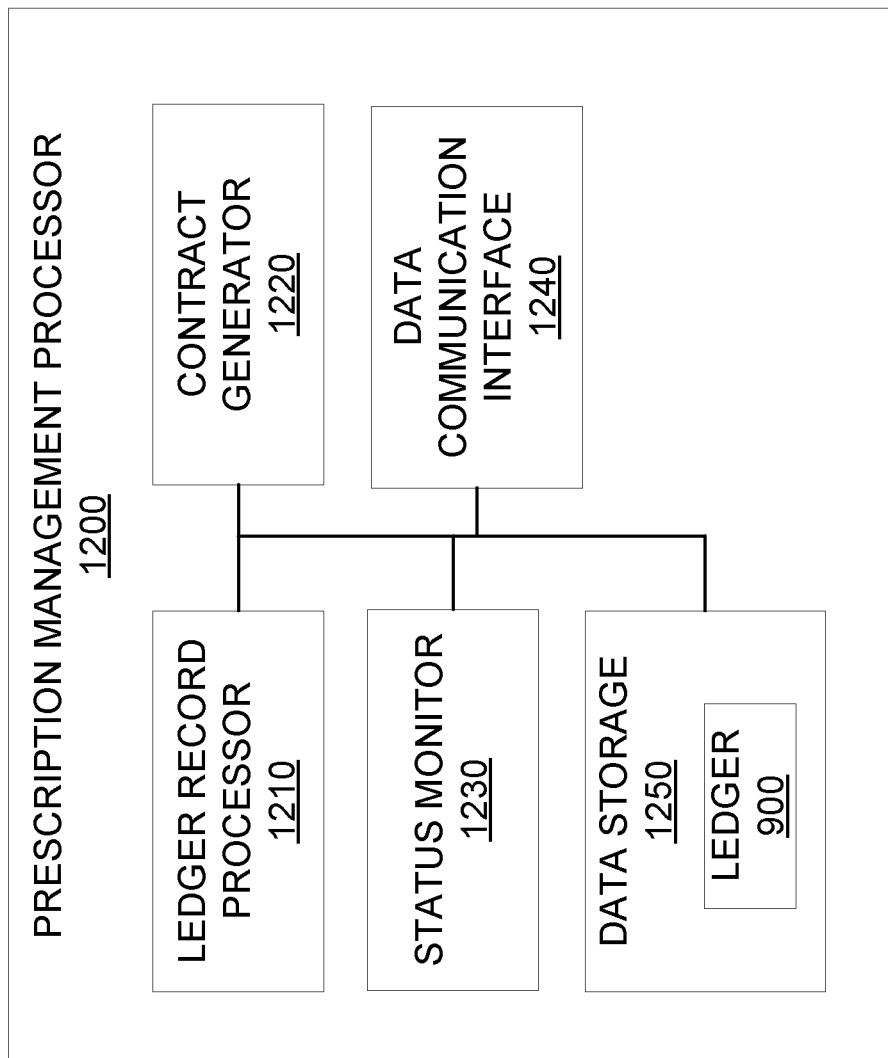
FIG. 12 illustrates an example schematic implementation of a prescription management processor.

FIG. 12 illustrates an example prescription management processor 1200 to manage a distributed ledger (e.g., the distributed ledger 800, 900, 1002) and facilitate processing, tracking, and updating of prescription information, patient treatment progress, instructions, updates, etc., via the distributed ledger. The example processor 1200 includes a ledger record processor 1210, a contract generator 1220, a status monitor 1230, a data communication interface 1240, and data storage 1250.

The example ledger record processor 1210 processes transactions involving records 810-830, 910-930 in the distributed ledger(s) 800, 900, 1002. The example processor 1210 can update the ledger 800, 900, 1002 in the data storage 1250 based on patient, device, new prescription, prescription activity, etc. The example contract generator 1220 can generate a smart contract (e.g., smart contract 1100, etc.) for prescription fulfillment, payment, management, etc. The example generator 1220 can interact with the ledger record processor 1210 to add the smart contract 1100 and/or a transaction involving the smart contract to the distributed ledger(s) 800, 900, 1002, for example. The example status monitor 1230 can monitor the administration of the prescription to the patient and/or other prescription status (e.g., amount remaining, insurance approval, copay status, funding status/amount, number of refills, frequency, etc.) and work with the ledger record processor 1210 to update the ledger 800, 900, 1002 based on a change in prescription status, for example. Information can be transmitted from the management processor 1200 and to the management processor 1200 via the data communication interface 1240 (e.g., a wired data communication interface and/or a wireless data communication interface such as a cellular communication interface, Wi-Fi communication interface, Bluetooth communication interface, near field communication interface, etc.). Data, including a copy of the distributed ledger 800, 900, 1002, can be stored in the data storage 1250 along with instructions, parameters, etc., for execution by the components of the processor 1200, for example.

Thus, using the example prescription management processor 1200 can be implemented separately and/or included in one or more of the blockchain network 310, prescribing computer system 320, insurer/primary care system 330, therapeutic/diagnostic overseer system 340, energy control system 360, pharmacy system 410, mobile computing device 420, etc., to generate, manage, update, maintain, etc., a prescription blockchain and/or other distributed ledger 800, 900, 1002, and associated transactions to help ensure accuracy, security, processability, and adherence to clinical protocol.

Figure 13:
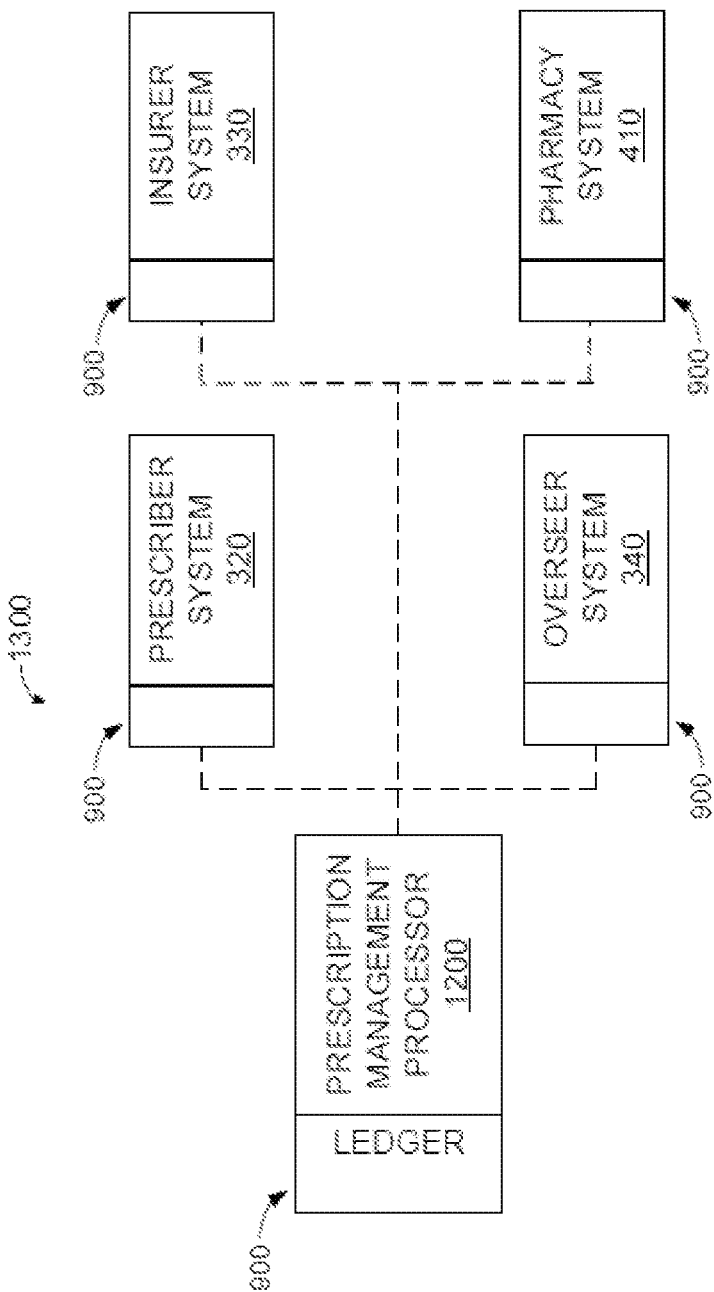
FIG. 13 shows an example peer-updated system including a distributed ledger.

FIG. 13 shows an example network 1300 (e.g., the blockchain network 310, etc.) in which the prescription management processor 1200 communicates with the prescriber system 320, the insurer system 330, the overseer system 340, and the pharmacy system 410 to exchange updates to the distributed ledger 900. In the example of FIG. 13, each system includes a copy of the ledger 900, and an update to a record 910-930 in the ledger 900 is to be propagated to each copy of the distributed ledger 900. Then a transaction and/or other update can be verified (e.g., automatically after every update, periodically after a time period and/or number of updates, manually at user/system request, etc.) against multiple copies of the ledger 900. If the update is isolated to only one copy of the ledger 900, then the update can be eliminated and/or investigated further as potentially fraudulent/erroneous, for example. Thus, in the example of FIG. 13, peer systems can provide feedback regarding record content, record updates, and transactions involving records, etc. In certain examples, the prescription management processor 1200 can be incorporated into one or more of the systems 320, 330, 340, 410 instead of or in addition to a separate processor.

While example implementations are illustrated in conjunction with FIGS. 1-13, elements, processes and/or devices illustrated in conjunction with FIGS. 1-13 may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts and/or data flows representative of example machine readable instructions for implementing components disclosed and described herein are shown in conjunction with at least FIGS. 1-13 is shown in the example of FIGS. 6, 10, and 14-15. In the examples, the machine readable instructions include a program for execution by a processor such as the processor 1612 shown in the example processor platform 1600 discussed below in connection with FIG. 16. The program may be embodied in machine readable instructions stored on a tangible computer readable storage medium such as a CD-ROM, a floppy disk, a hard drive, a digital versatile disk (DVD), a Blu-ray disk, or a memory associated with the processor 1612, but the entire program and/or parts thereof could alternatively be executed by a device other than the processor 1612 and/or embodied in firmware or dedicated hardware. Further, although the example program is described with reference to the flowcharts illustrated in conjunction with at least FIGS. 6, 10, and 14-15, many other methods of implementing the components disclosed and described herein may alternatively be used. For example, the order of execution of the blocks may be changed, and/or some of the blocks described may be changed, eliminated, or combined. Although the flowcharts and/or data flows of at least FIGS. 6, 10 and 14-15 depict example operations in an illustrated order, these operations are not exhaustive and are not limited to the illustrated order. In addition, various changes and modifications may be made by one skilled in the art within the spirit and scope of the disclosure. For example, blocks illustrated in the flowcharts may be performed in an alternative order or may be performed in parallel.

As mentioned above, the example process(es) of at least FIGS. 6, 10, and 14-15 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of at least FIGS. 6, 10, and 14-15 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 14:
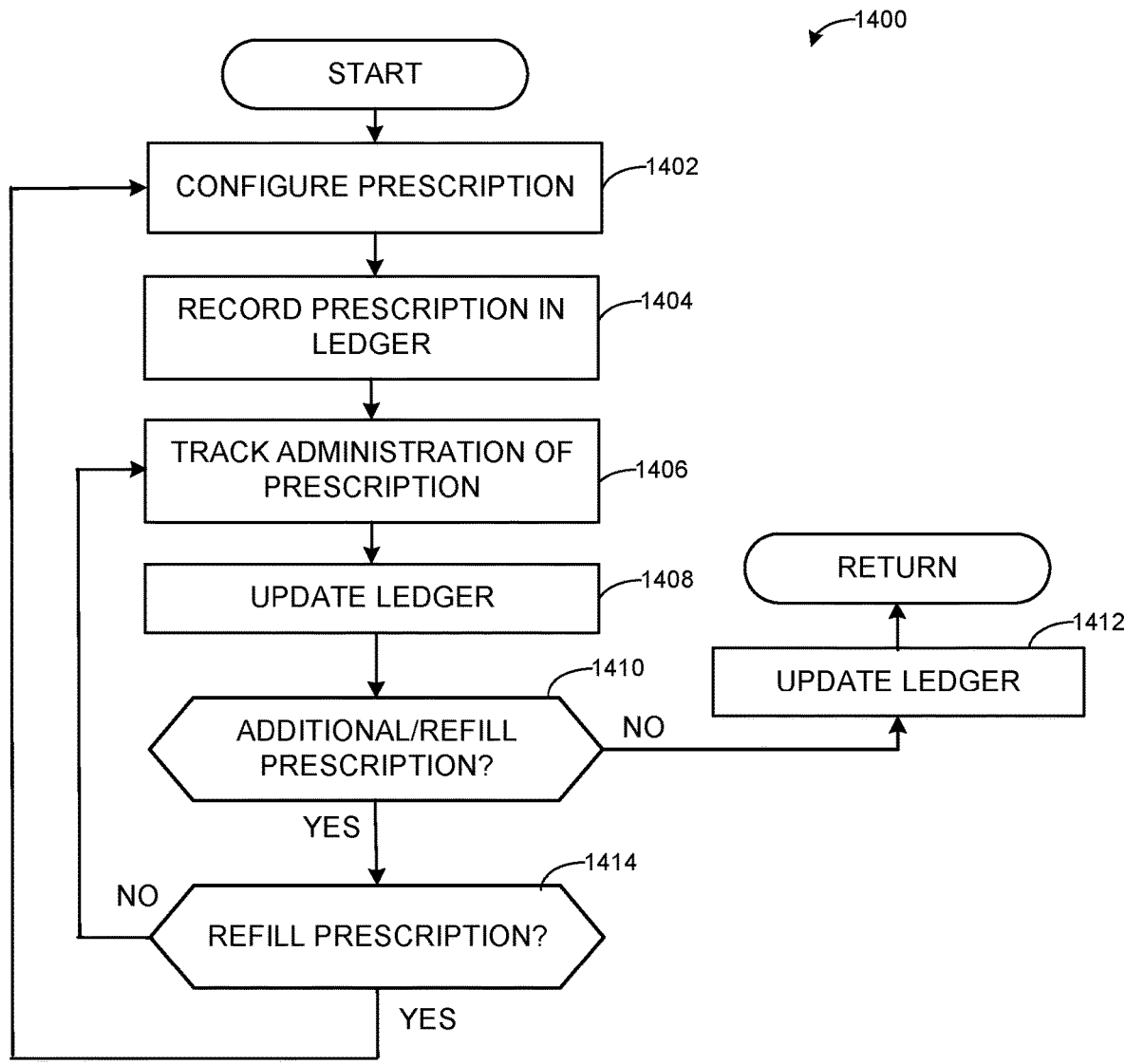
FIGS. 14-15 illustrate flow diagrams of example methods to manage prescriptions.

FIG. 14 illustrates a flow diagram of an example method 1400 to manage an electronic prescription defining an action for a patient. The electronic prescription can be a logical data structure, such as one or more records in a blockchain and/or other distributed ledger, etc., to configure a device to apply the action (e.g., energy therapy, ultrasound imaging, medication, other stimulus, etc.) to a patient according to the prescription, for example. At block 1402, a prescription is configured for a patient. For example, a device (e.g., the energy application device 370 and/or other device represented by the device construct 605, etc.) is configured in a device prescription to apply an action (e.g., application of energy, ultrasound imaging, administering pharmaceutical medication, etc.) to a patient. Additionally, payment information associated with the action, including insurance coverage, patient copayment, etc., can be determined as part of the prescription, for example. Parameters and/or settings of the action and/or associated device such as amount, frequency, strength/intensity/dose, verification, etc., can be set according to clinical guidelines, treatment and/or diagnostic protocol, clinician input, etc.

At block 1404, the configured prescription is recorded in the distributed ledger 800, 900, 1002. For example, the configured prescription is added as a record 910-930 in the distributed ledger 900, added as an update to existing record 910-930 in the distributed ledger 900, etc. Thus, the logical data structure of the configured prescription construct is maintained and distributed across multiple devices/systems acting as nodes in a distributed ledger network via copies of the distributed ledger 800, 900, 1002 stored at participating nodes, for example.

At block 1406, administration of the prescription is tracked/monitored. For example, the prescription management processor 1200, running on a separate processor and/or implemented in conjunction with the prescriber system 320, insurer system 330, overseer system 340, pharmacy system 410, mobile device 420, etc., can monitor administration of the prescription to the patient, such as delivery of energy therapy to the patient 380 via the energy device 370, administration of pharmaceutical medication to the patient (e.g., via a needle, catheter, other delivery device, etc.), administration of radiopharmaceutical material to the patient, etc. Tracking prescription administration can also include tracking dispensation of payment to the pharmacy system 410 and/or other provider as the prescription material is being administered to the patient. Thus, the patient can dynamically pay by the dose, pay when administration begins, pay when administration ends, etc., and the provider can be paid without delay or lag time for further insurance approval, billing, etc.

At block 1408, the distributed ledger 800, 900, 10002 with an updated and/or new record 810-830, 910-930 to reflect the prescription administration, other change in prescription status, etc. For example, the prescription management processor 1200 can update the ledger 800, 900, 1002 and propagate changes to copies of the distributed ledger 800, 900, 1002 maintained by a plurality of devices/systems 320-420. In certain examples, updating the ledger 800, 900, 1002 includes verifying the update by comparing multiple copies of the ledger 800, 900, 1002 distributed among a plurality of systems 320-420, performing hashing and/or other proof of work algorithm to verify that a device/system 320-420 is authorized to add to the distributed ledger 800, 900, 1002, etc.

At block 1410, a state or status of the prescription is evaluated to determine whether the prescription is exhausted, not yet exhausted, and/or is to be refilled. If the prescription is exhausted and/or otherwise finished, then, at block 1412, the ledger 800, 900, 1002 is updated to reflect completion of the prescription, and the program ends/returns. However, if material remains in the prescription or if the prescription is empty but a refill is ordered/triggered/added, etc., then control shifts to block 1414. At block 1414, the continuation of the prescription is evaluated to determine whether the prescription is to be refilled or if administration is to continue with the current prescription. If administration of the current prescription material is to continue (e.g., more material/instruction remaining, no refill warranted, etc.), then control reverts to block 1406 to continue monitoring prescription administration. If a refill of the prescription is warranted (e.g., more material, new instruction for action, etc.), then control reverts to block 1402 to adjust/configure/manage the prescription for the refill. For example, new authorization, payment, settings, etc., may be involved in refilling the prescription and updating one or more records 810-830, 910-930*b* of the distributed ledger 800, 900, 1002, such as verification, etc.

Thus, the prescription can be a device prescription to configure a device to apply an action to a patient, a pharmaceutical prescription for particular medicine/material to be administered to the patient, a monitoring prescription to configure the device to monitor the patient (e.g., using sensors, imaging, electrocardiogram, etc.), and/or an examination prescription to configure the device for examination of the patient (e.g., using sensors, imaging, electrocardiogram, computer-aided detection, etc.), etc.

Figure 15:
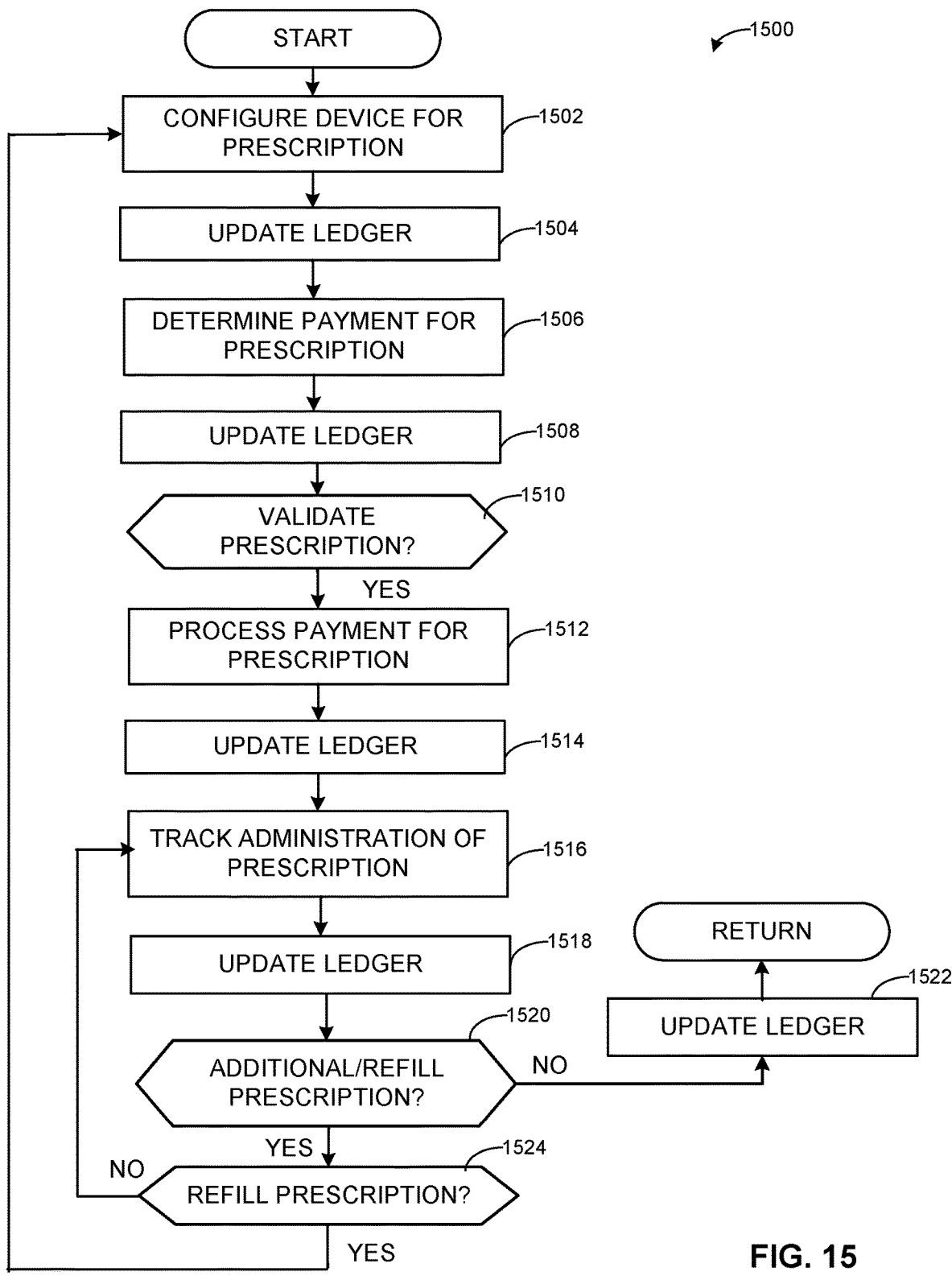

FIG. 15 illustrates an example implementation 1500 of the example process 1400 for prescription management. The electronic prescription can be a logical data structure, such as one or more records in a blockchain and/or other distributed ledger, etc., to configure a device to apply the action (e.g., energy therapy, ultrasound imaging, medication, other stimulus, etc.) to a patient according to the prescription, for example. At block 1502, an electronic prescription is configured for execution with respect to a patient by configuring a device (e.g., a device prescription configuring the energy application device 370 and/or other device represented by the device construct 605, etc.) to apply an action (e.g., application of energy, ultrasound imaging, administering pharmaceutical medication, etc.) to the patient. For example, parameters and/or settings of the action and/or associated device such as amount, frequency, strength/intensity/dose, verification, etc., can be set according to clinical guidelines, treatment and/or diagnostic protocol, clinician input, etc. At block 1504, a distributed ledger 800, 900, 1002 is updated with the device configuration information. For example, a new record 810-830, 910-930 can be added and/or existing record 810-830, 910-930 can be updated with a transaction providing the device configuration information for the prescription. At block 1506, payment information associated with the action, including insurance coverage, patient copayment, etc., is determined as part of the prescription, for example. At block 1508, the payment information is recorded as a transaction associated with a new and/or updated record 810-830, 910-930 in the distributed ledger 800, 900, 1002.

At block 1510, the action to be applied to the patient through the prescription is validated using the distributed ledger 800, 900, 1002. For example, one or more systems 320-420, 1200 storing and/or accessing a copy of the distributed ledger 800, 900, 1002 can compare record 810-830, 910-930 information to verify the content of the prescription and its associated action(s). A value comparison can help ensure accuracy/consistency, and/or a hashing and/or other proof of work function can verify that a system 320-420, 1200 is authorized to add/adjust a record 810-830, 910-930 in the distributed ledger 800, 900, 1002. Thus, the logical data structure of the configured prescription construct is maintained and distributed across multiple devices/systems acting as nodes in a distributed ledger network via copies of the distributed ledger 800, 900, 1002 stored at participating nodes, for example.

At block 1512, when the action is validated, payment for the action is processed using the payment information in the prescription. For example, payment including insurance payment information, patient copay, etc., can be applied when the electronic prescription is processed by the device to apply the action to the patient. At block 1514, the distributed ledger 800, 900, 1002 is updated to reflect the payment and/or action. For example, one or more systems/devices 320-420, 1200 can propagate a record 810-830, 910-939 of at least one of i) the payment or ii) the action to the distributed ledger 800, 900, 1002.

At block 1516, administration of the prescription is tracked/monitored. For example, the prescription management processor 1200, running on a separate processor and/or implemented in conjunction with the prescriber system 320, insurer system 330, overseer system 340, pharmacy system 410, mobile device 420, etc., can monitor administration of the prescription to the patient, such as delivery of energy therapy to the patient 380 via the energy device 370, administration of pharmaceutical medication to the patient (e.g., via a needle, catheter, other delivery device, etc.), administration of radiopharmaceutical material to the patient, etc. Tracking prescription administration can also include tracking dispensation of payment to the pharmacy system 410 and/or other provider as the prescription material is being administered to the patient. Thus, the patient can dynamically pay by the dose, pay when administration begins, pay when administration ends, etc., and the provider can be paid without delay or lag time for further insurance approval, billing, etc.

At block 1518, the distributed ledger 800, 900, 10002 with an updated and/or new record 810-830, 910-930 to reflect the prescription administration, other change in prescription status, etc. For example, the prescription management processor 1200 can update the ledger 800, 900, 1002 and propagate changes to copies of the distributed ledger 800, 900, 1002 maintained by a plurality of devices/systems 320-420. In certain examples, updating the ledger 800, 900, 1002 includes verifying the update by comparing multiple copies of the ledger 800, 900, 1002 distributed among a plurality of systems 320-420, performing hashing and/or other proof of work algorithm to verify that a device/system 320-420 is authorized to add to the distributed ledger 800, 900, 1002, etc.

At block 1520, a state or status of the prescription is evaluated to determine whether the prescription is exhausted, not yet exhausted, and/or is to be refilled. If the prescription is exhausted and/or otherwise finished, then, at block 1522, the ledger 800, 900, 1002 is updated to reflect completion of the prescription, and the program ends/returns. However, if material remains in the prescription or if the prescription is empty but a refill is ordered/triggered/added, etc., then control shifts to block 1524. At block 1524, the continuation of the prescription is evaluated to determine whether the prescription is to be refilled or if administration is to continue with the current prescription. If administration of the current prescription material is to continue (e.g., more material/instruction remaining, no refill warranted, etc.), then control reverts to block 1526 to continue monitoring prescription administration. If a refill of the prescription is warranted (e.g., more material, new instruction for action, etc.), then control reverts to block 1502 to adjust/configure/manage the prescription for the refill. For example, new authorization, payment, settings, etc., may be involved in refilling the prescription and updating one or more records 810-830, 910-930b of the distributed ledger 800, 900, 1002, such as verification, etc.

Figure 16:
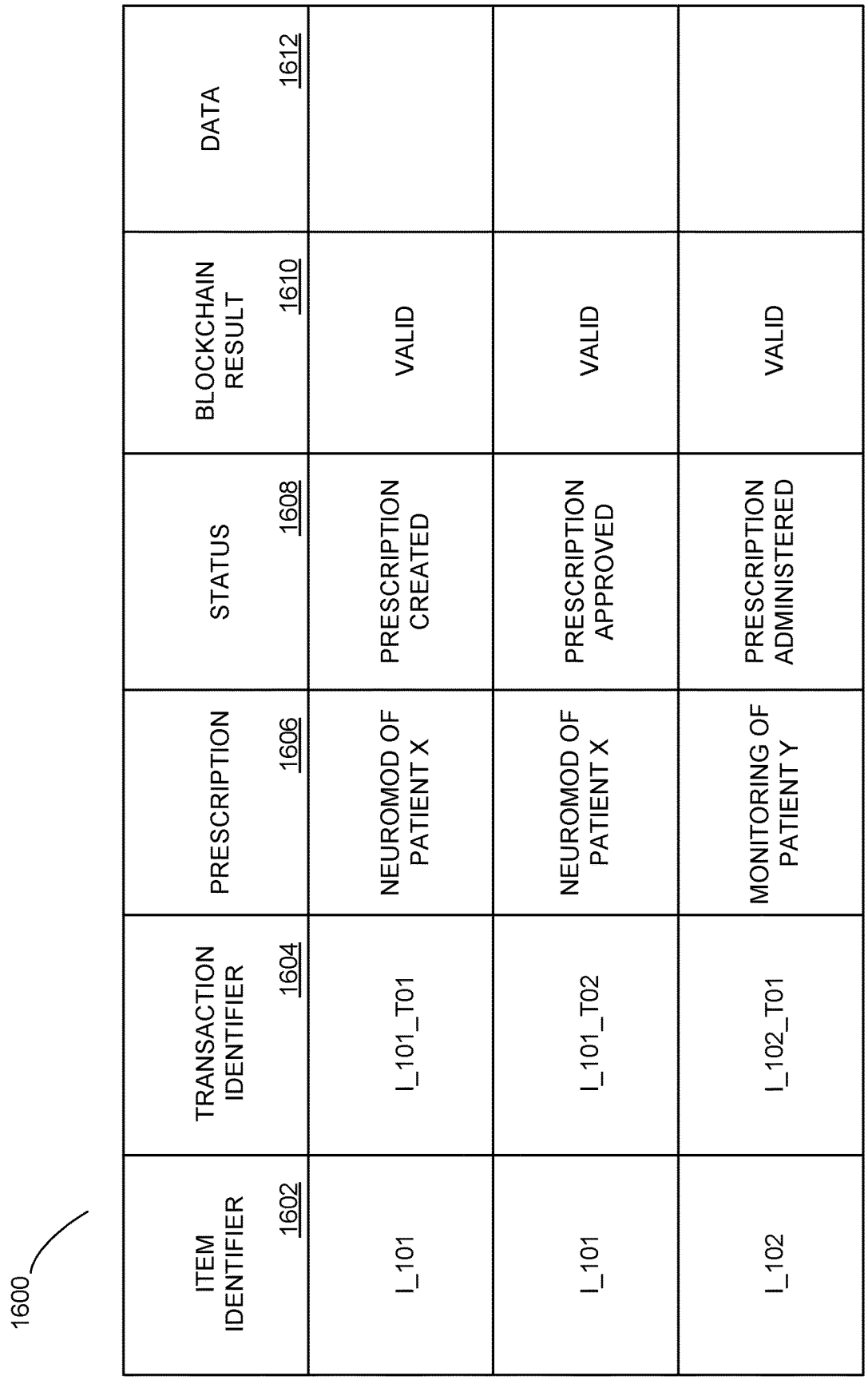
FIG. 16 depicts an example table to store digital prescription and blockchain transaction information.

While certain example records, systems, and associated methods have been disclosed above, other record formats and associated systems and methods can be used for prescription and associated device management. For example, FIG. 16 illustrates an example table 1600 that represents stored electronic prescription information for processing by the example system 300, 400, etc. The table 1600 can include entries identifying electronic prescriptions and associated transactions with respect to the prescriptions. The example table 1600 can define a plurality of fields including an item identifier 1602, a transaction identifier 1604, prescription information 1606, a status 1608, a blockchain results 1610, and data 1612. Using the example table 1600, digital prescription information can be tracked for one or more patients, users, equipment, etc. The example item identifier 1602 can be used to identify the patient, user, equipment, and/or other record in question, for example, using a unique alphanumeric code, and the transaction identifiers 1604 can be used to record transactions, events, and/or other stages of prescription generation, authorization, delivery, and refill, for example. The prescription information 1606 can be used to identify some or all information regarding the prescription (e.g., equipment, dosage, other setting, etc.). The status 1608 can be used to indicate whether the prescription is approved, rejected, awaiting approval, delivered/administered, expired/empty, refilled, etc., and the blockchain result 1610 can be used to indicate whether some or all of the information for the digital prescription has been verified via a distributed ledger (e.g., by comparing values between copies of the distributed ledger, by executing a proof of work with respect to the distributed ledger, etc.). The data 1612 can include bits of information to define the associated prescription information 1606, for example. Thus, prescriptions and associated status, event, etc., can be tracked via the table or container 1600, for example.

Figure 17:
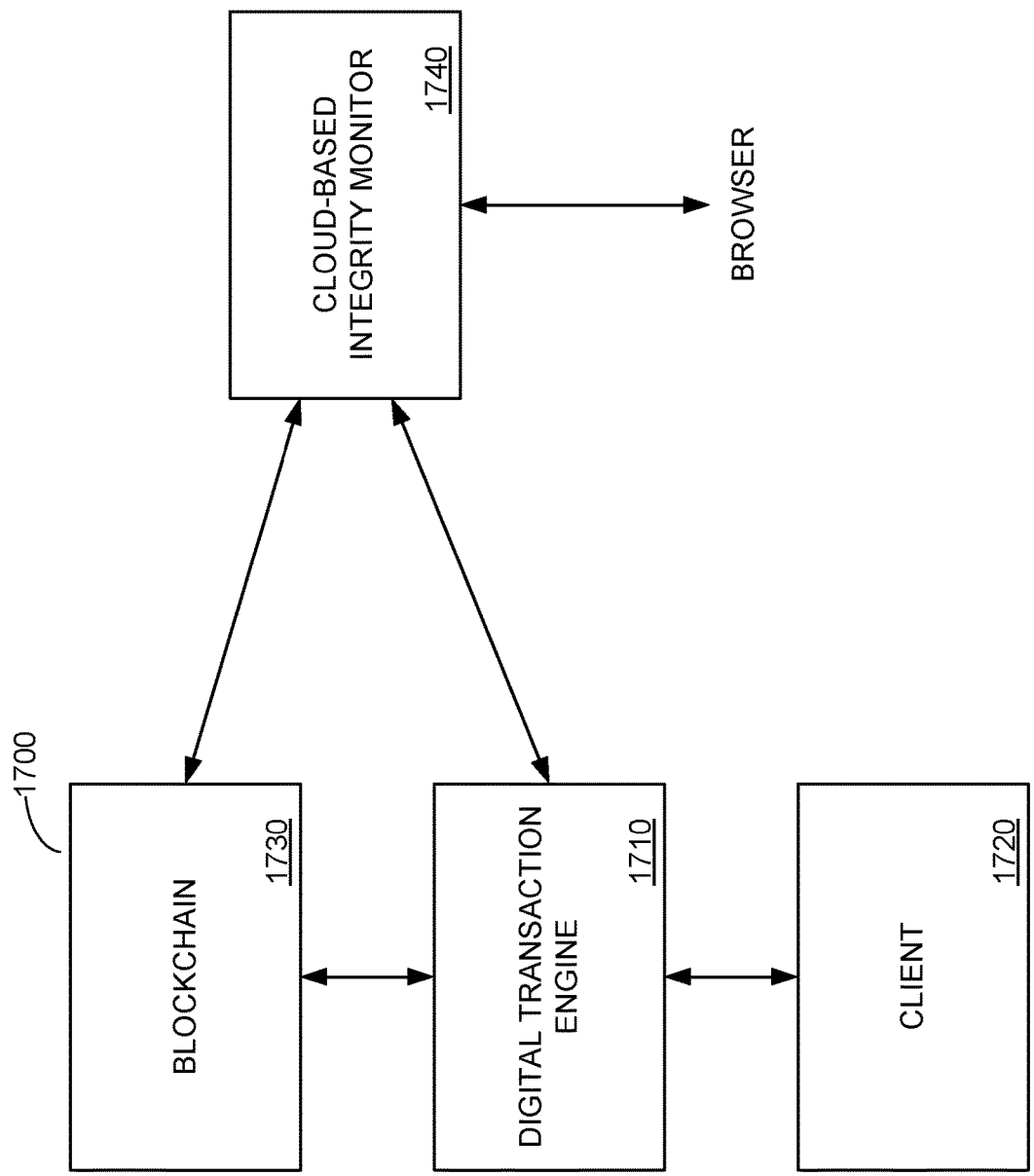
FIGS. 17-19 illustrate example distributed ledger processing systems.

In some examples, information associated with a digital prescription is recorded via a secure, distributed transaction ledger (e.g., associated with blockchain technology). For example, FIG. 17 is a system 1700 incorporating a secure, distributed transaction ledger. The system includes a digital transaction engine 1710 with a communication port to exchange information between a client 1720 and a blockchain 1730. For example, the digital transaction engine 1710 and/or other elements of the system 1700 can record information regarding a transaction with respect to the client and/or an associated digital prescription using the blockchain 1730 and/or other secure, distributed transaction ledger 1730 (e.g., via a blockchain verification process). For example, the digital transaction engine 1710 can record an order date and time, a price, a fill date, an approval, a refill, a dispensation/delivery, a compressed item definition file, etc., via the secure, distributed transaction ledger 1730 in accordance with any of the examples described herein. According to some examples, the distributed ledger 1730 can be associated with the HYPERLEDGER® blockchain verification system. Note that the digital transaction engine 1710 can be de-centralized and/or might be associated with a third party, such as a vendor that performs a service for an enterprise, for example. Transactions can be encoded into one or more segments and, according to some examples, information about transactions can be recorded using blockchain technology.

Figure 18:
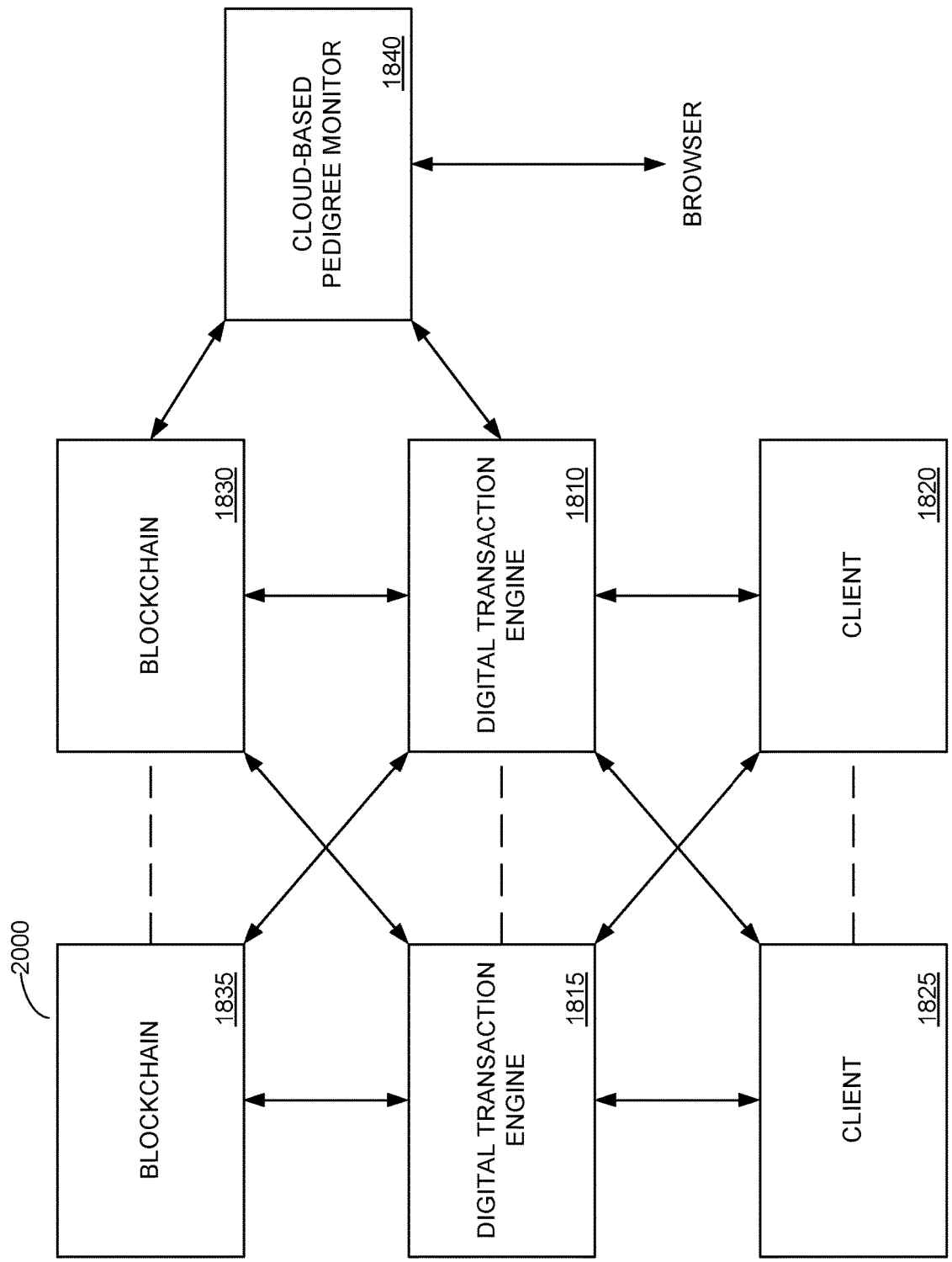

In certain examples, such as shown in the system 1700 of FIG. 17, a cloud-based integrity monitor 1740 can provide transaction integrity data via a web browser and exchange information with the blockchain 1730 and the digital transaction engine 1710 via Representational State Transfer ("REST") web services. The REST web services can, for example, provide interoperability between computer systems on the Internet (e.g., by allowing requesting systems to access and manipulate textual representations of web resources using a uniform, predefined set of stateless operations). In some examples, portions of the digital transaction engine 1710 can be associated with a MySQL database. In this way, the digital transaction engine 1710 and blockchain 1730 can be used to provide transaction level verification for the client 1720. Although FIG. 17 illustrates an example system 1700 with a single blockchain 1730, client 1720, and digital transaction engine 1710, note that other examples can employ other topologies. For example, FIG. 18 is a system 1800 implementing digital prescription management incorporating multiple digital transaction engines 1810-1815. In particular, an additional blockchain 1835 and digital transaction engine 1815 can provide protection for an additional client 1825. As illustrated in the example of FIG. 18, each digital transaction engine 1810, 1815 can be associated with multiple blockchains 1830, 1835 providing additional protection for the system 1800 (e.g., by storing information at multiple, geographically disperse nodes making attacks impractical). That is, each verifier (e.g., a digital transaction engine 1810-1815) can commit a brief summary to an independent data store and, once recorded, the information cannot be changed without detection to provide a tamper-proof System of Records ("SoR").

Note that different types and/or amounts of information might be recorded in a secure, distributed ledger. For example, data might be stored on a prescription-by-prescription basis, an event-by-event basis, a base prescription along with all associated dependent prescription changes, etc. Moreover, information about particular medical devices, other equipment, dosage, material, customer, patient, platform, payment, quality review process or result, etc., can be stored via a secure distributed ledger (e.g., using blockchain technology, etc.).

Figure 19:
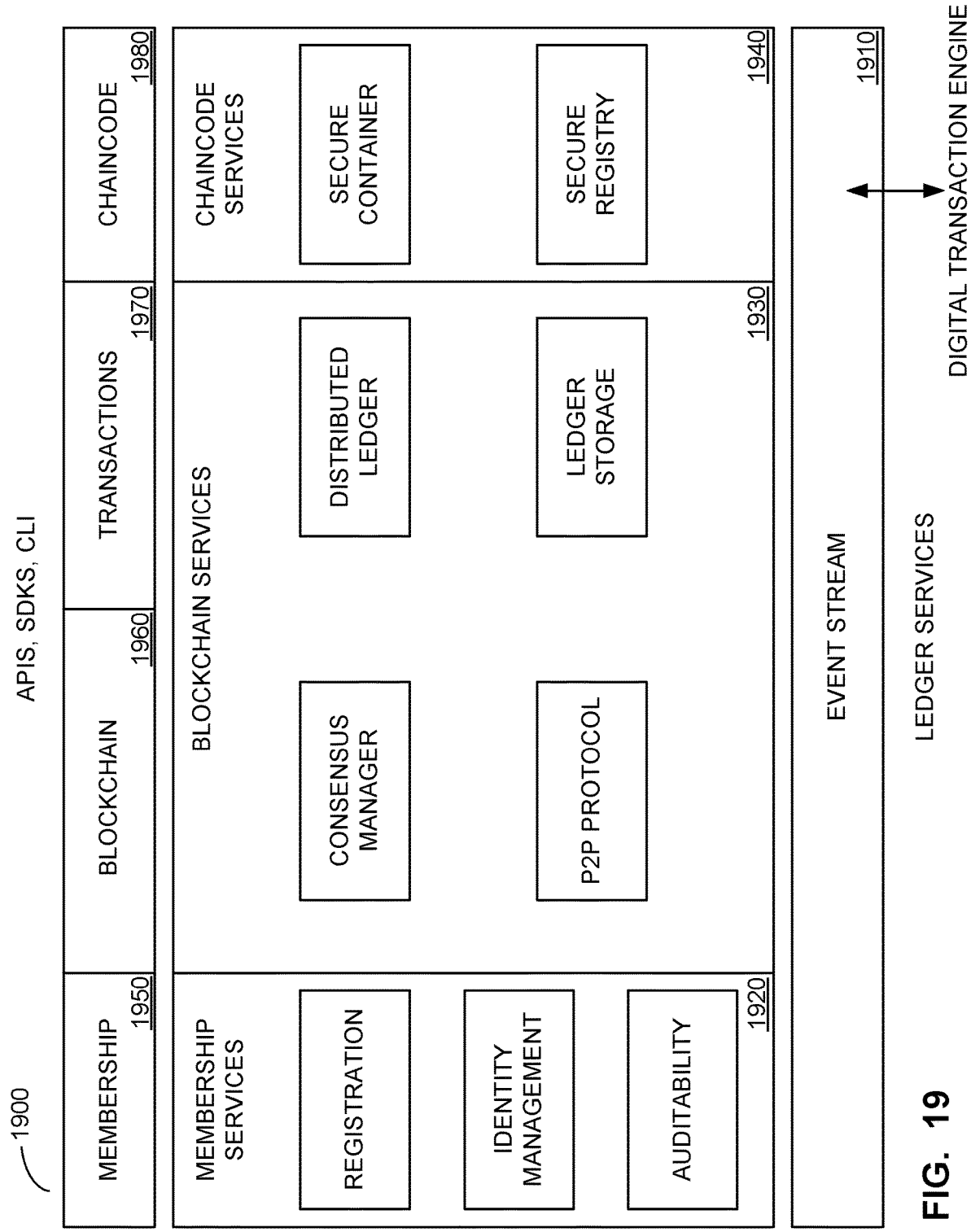

Examples disclosed herein can be associated with any type of distributed ledger having a de-centralized consensus-based network that supports smart contracts, digital assets, record repositories, and/or cryptographic security, for example. For example, FIG. 19 is a distributed ledger reference architecture 1900. The example architecture 1900 includes ledger services and an event stream 1910 that can include network security service information (e.g., from a first entity device). Membership services 1920 (e.g., including registration, identity managements, and/or an auditability process, etc.) can manage identity, privacy, and confidentiality for membership 1950 for the network security service.

Blockchain services 1930 (e.g., including a consensus manager, Peer-to-Peer ("P2P") protocol, a distributed ledger, and/or ledger storage, etc.) can manage the distributed ledger through a P2P protocol to maintain a single state that is replicated at many nodes to support blockchains 1960 and transactions 1970. Chaincode services 1940 (e.g., secure container and/or a secure registry associated with a smart contract) can help compartmentalize smart contract (or chaincode 1980) execution on validating nodes. Note that the environment may be a "locked down", secured container with a set of signed base images that contain a secure operating system and programming language(s). In certain examples, application programming interfaces (APIs), Software Development Kits (SDKs), and/or a Command Line Interface (CLI) can be utilized to support a network security service via the reference architecture 1900.

Figure 20:
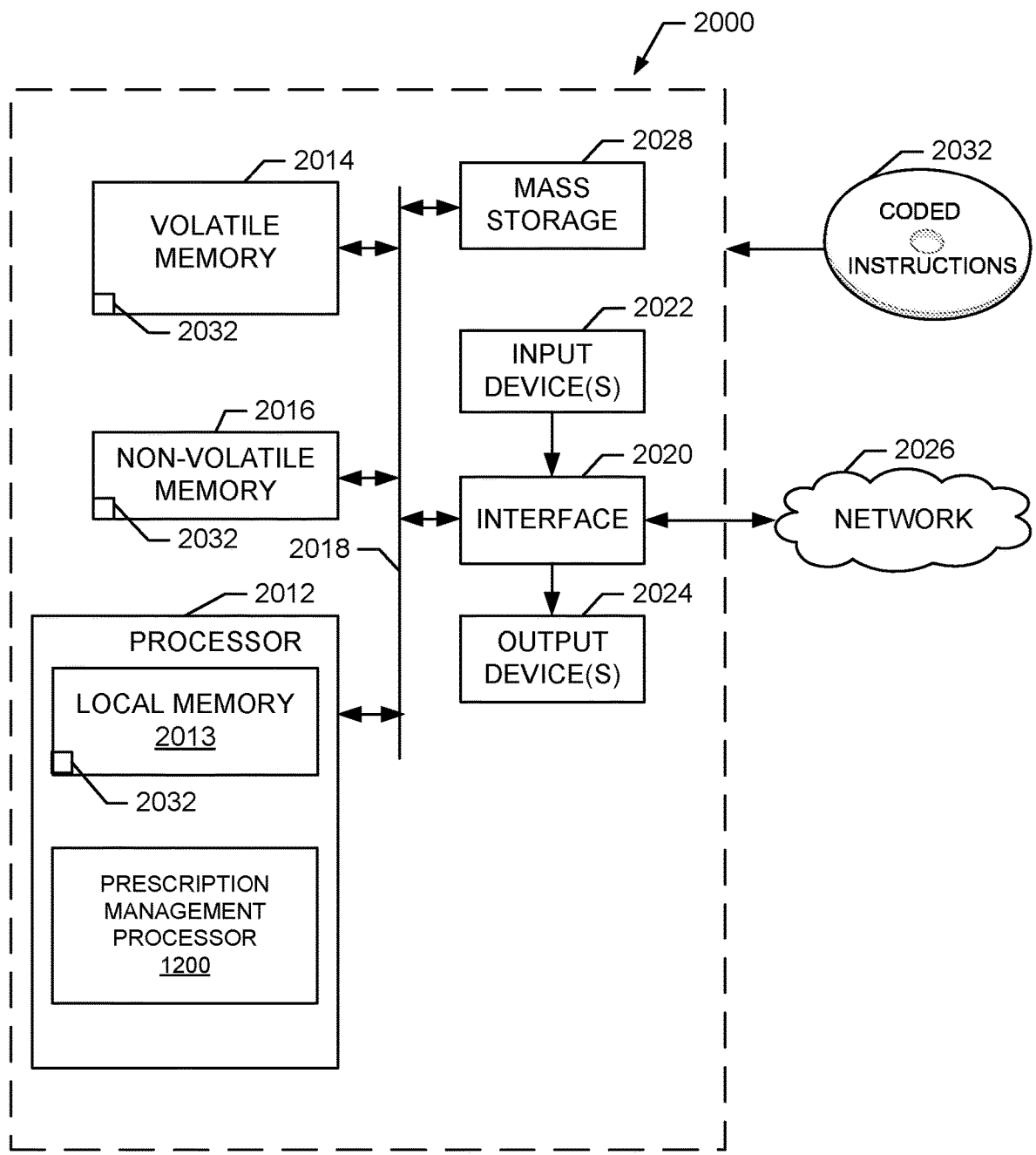
FIG. 20 is a block diagram of a processor platform structured to execute the example machine readable instructions to implement components disclosed and described herein.

FIG. 20 is a block diagram of an example processor platform 2000 structured to executing the instructions of at least FIGS. 6, 10, and 14-15 to implement the example components disclosed and described herein with respect to FIGS. 1-19. The processor platform 2000 can be, for example, a server, a personal computer, a mobile device (e.g., a cell phone, a smart phone, a tablet such as an iPad™), a personal digital assistant (PDA), an Internet appliance, or any other type of computing device.

The processor platform 2000 of the illustrated example includes a processor 2012. The processor 2012 of the illustrated example is hardware. For example, the processor 2012 can be implemented by integrated circuits, logic circuits, microprocessors or controllers from any desired family or manufacturer.

The processor 2012 of the illustrated example includes a local memory 2013 (e.g., a cache). The example processor 2012 of FIG. 20 executes the instructions of at least FIGS. 6, 10, and 14-15 to implement the systems and infrastructure and associated methods of FIGS. 1-19 such as the example prescriber system 320, the example insurer system 330, the example overseer system 340, the example pharmacy system 410, the example mobile computing device 420, the example distributed ledger 800, 900, 1002, the example smart contract 1100, the example prescription management processor 1200, the example system/architecture 1700-1900, etc. The processor 2012 of the illustrated example is in communication with a main memory including a volatile memory 2014 and a non-volatile memory 2016 via a bus 2018. The volatile memory 2014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2016 may be implemented by flash memory and/or any other desired type of memory device. Access to the main memory 2014, 2016 is controlled by a clock controller.

The processor platform 2000 of the illustrated example also includes an interface circuit 2020. The interface circuit 2020 may be implemented by any type of interface standard, such as an Ethernet interface, a universal serial bus (USB), and/or a PCI express interface.

In the illustrated example, one or more input devices 2022 are connected to the interface circuit 2020. The input device(s) 2022 permit(s) a user to enter data and commands into the processor 2012. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 2024 are also connected to the interface circuit 2020 of the illustrated example. The output devices 2024 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 2020 of the illustrated example, thus, typically includes a graphics driver card, a graphics driver chip or a graphics driver processor.

The interface circuit 2020 of the illustrated example also includes a communication device such as a transmitter, a receiver, a transceiver, a modem and/or network interface card to facilitate exchange of data with external machines (e.g., computing devices of any kind) via a network 2026 (e.g., an Ethernet connection, a digital subscriber line (DSL), a telephone line, coaxial cable, a cellular telephone system, etc.).

The processor platform 2000 of the illustrated example also includes one or more mass storage devices 2028 for storing software and/or data. Examples of such mass storage devices 2028 include floppy disk drives, hard drive disks, compact disk drives, Blu-ray disk drives, RAID systems, and digital versatile disk (DVD) drives.

The coded instructions 2032 of FIG. 20 may be stored in the mass storage device 2028, in the volatile memory 2014, in the non-volatile memory 2016, and/or on a removable tangible computer readable storage medium such as a CD or DVD.

Figure 21:
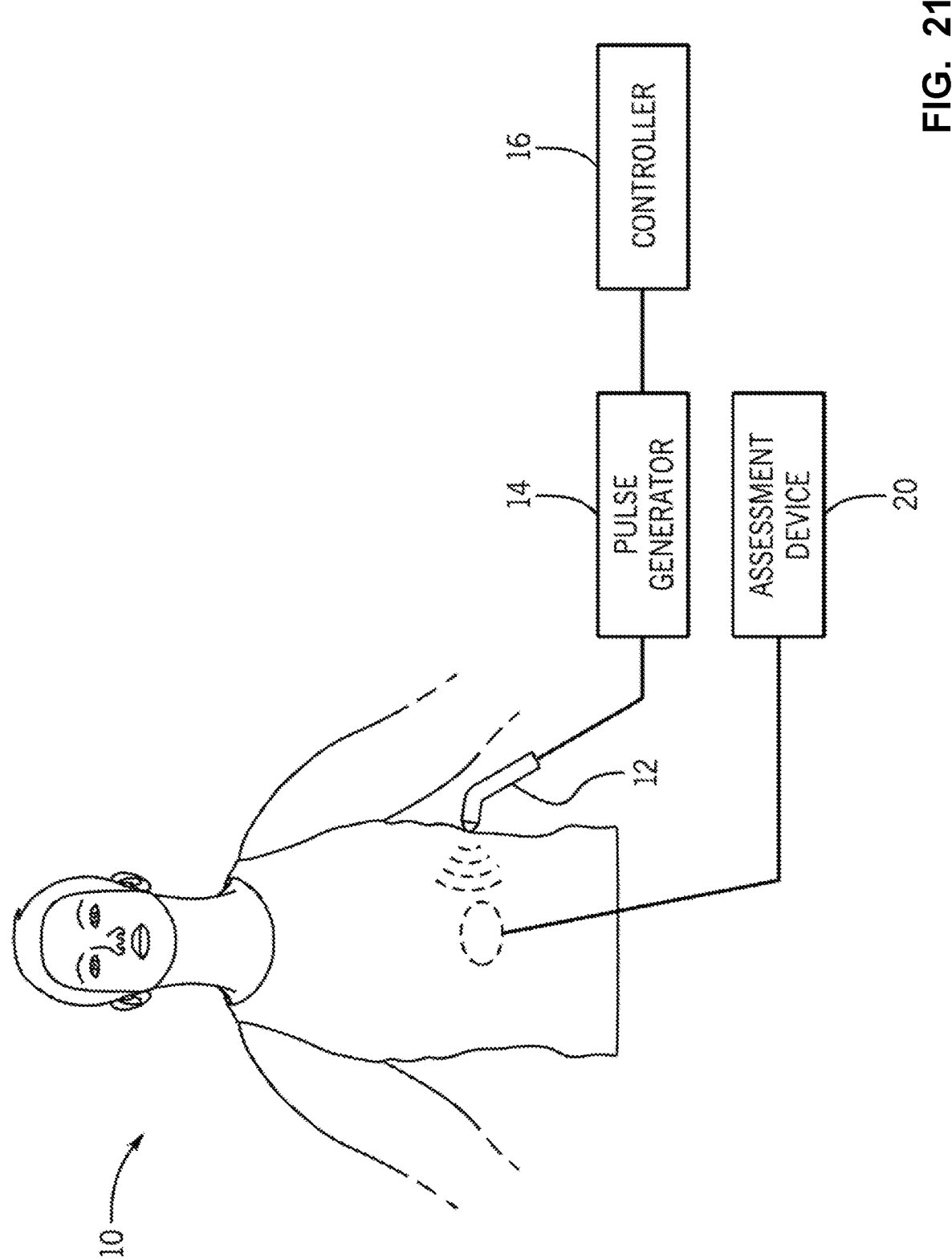
FIGS. 21-22 illustrate an example ultrasound modulation system incorporating the example processor platform of FIG. 20.

In certain examples, the processor platform 2000 can be implemented in an ultrasound imaging system and/or neuromodulation device. FIG. 21 illustrates an example ultrasound neuromodulation system 10 to deliver focused ultrasound to a patient in accordance with a digital prescription. To that end, the disclosed distributed ledger systems and methods can be used in conjunction with the neuromodulation system 10.

FIG. 21 is a schematic representation of a system 10 for neuromodulation to achieve neurotransmitter release according to a digital prescription maintained using a distributed ledger. The example system 10 includes a pulse generator 14 coupled to an energy application device 12 (e.g., an ultrasound transducer). The energy application device 12 is configured to receive energy pulses, such as via leads or wireless connection, that in use are directed to a region of interest of an internal tissue or an organ of a subject, which in turn results in a targeted physiological outcome. In certain examples, the pulse generator 14 and/or the energy application device 12 can be implanted and/or otherwise positioned at a biocompatible site (e.g., the abdomen, etc.), and the lead or leads couple the energy application device 12 and the pulse generator 14 internally. For example, the energy application device 12 can be a MEMS transducer, such as a capacitive micromachined ultrasound transducer.

In certain examples, the energy application device 12 and/or the pulse generator 14 can communicate wirelessly, for example with a controller 16 that in turn provides instructions to the pulse generator 14. In other examples, the pulse generator 14 can be an extracorporeal device (e.g., may operate to apply energy transdermally or in a noninvasive manner from a position outside of a subject's body) and can, in certain examples, be integrated within the controller 16. In examples in which the pulse generator 14 is extracorporeal, the energy application device 12 can be operated by a caregiver and positioned at a spot on or above a subject's skin such that the energy pulses are delivered transdermally to a desired internal tissue, for example. Once positioned to apply energy pulses to the desired site, the system 10 can initiate neuromodulation (e.g., according to a dosage, time period or interval, etc., specified in a digital prescription, etc.) to achieve targeted physiological outcome or clinical effects.

In certain examples, the system 10 can include an assessment device 20 that is coupled to the controller 16 and assesses characteristics that are indicative of whether the targeted physiological outcome of the modulation has been achieved. In an example, the targeted physiological outcome can be local. For example, the modulation can result in local tissue or function changes, such as tissue structure changes, local increase in concentration of certain molecules, tissue displacement, increased fluid movement, etc. The modulation can result in systemic or non-local changes, and the targeted physiological outcome can be related to a change in concentration of circulating molecules or a change in a characteristic of a tissue that does not include the region of interest to which energy was directly applied, for example. In an example, the displacement is a proxy measurement for a successful modulation, and displacement measurements below an expected displacement value can result in modification of modulation parameters until expected displacement value is observed.

The system 10, as provided herein, can provide energy pulses according to various modulation parameters. For example, the modulation parameters can include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters can also include frequency and duration of a stimulation application. The application frequency can be continuous or delivered at various time periods, for example, within a day or week. The treatment duration can last for various time periods, including, but not limited to, from a few minutes to several hours. In certain examples, treatment duration with a specified stimulation pattern may last for a certain interval (e.g., one hour, etc.) and is repeated at certain intervals (e.g., 72 hour intervals, etc.). In certain examples, treatment can be delivered at a higher frequency (e.g., every three hours, etc.) for shorter durations (e.g., 30 minutes, 45 minutes, etc.). The treatment duration and frequency can be adjustably controlled to achieve a desired result.

Figure 22:
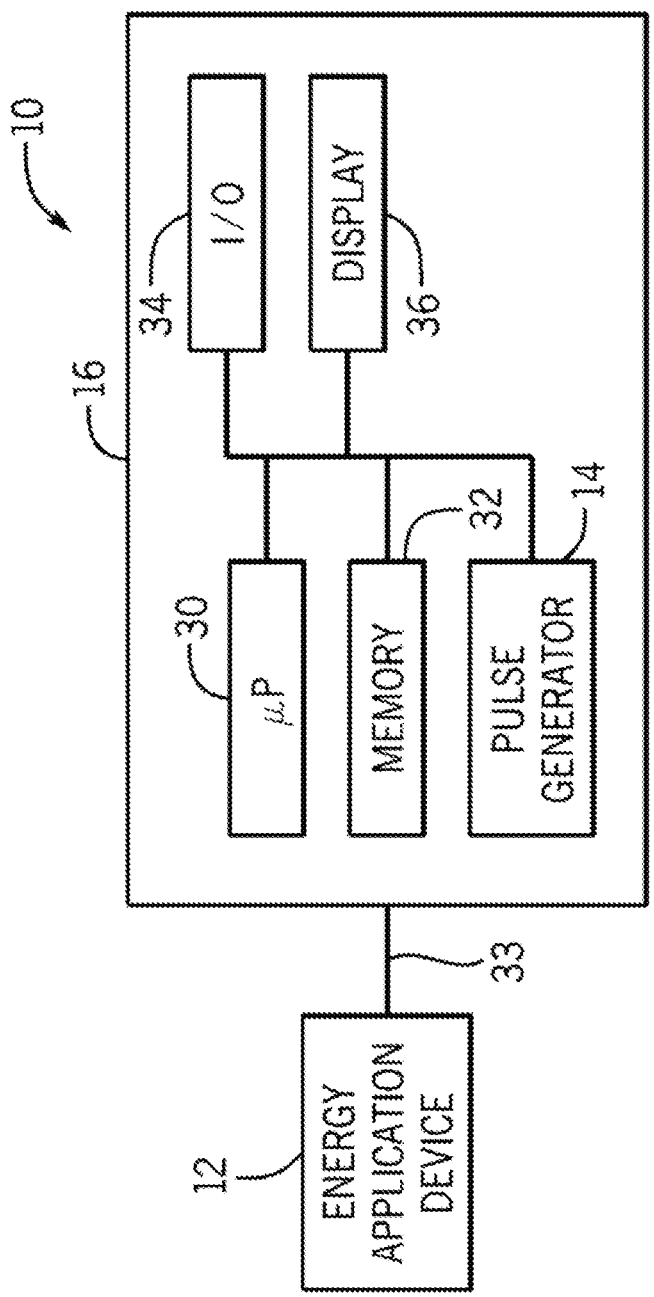

FIG. 22 is a block diagram of certain components of the system 10. As provided herein, the system 10 for neuromodulation can include a pulse generator 14 that is adapted to generate a plurality of energy pulses for application to a tissue of a subject. The pulse generator 14 can be separate and/or integrated into an external device, such as a controller 16. The controller 16 includes a processor 30 for controlling the device. Software code or instructions are stored in memory 32 of the controller 16 for execution by the processor 30 to control the various components of the device. A copy of a blockchain and/or other distributed ledger 800, 900, 1730, 1830, 1835 can be stored in memory 32 and updated by the controller 16 as well, for example. The controller 16 and/or the pulse generator 14 can be connected to the energy application device 12 via one or more leads 33, for example.

The controller 16 also includes a user interface with input/output circuitry 34 and a display 36 that are adapted to allow a clinician to provide selection inputs or modulation parameters to modulation programs. Each modulation program can include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to the subject. Any suitable type of pulse generating circuitry can be employed including constant current, constant voltage, multiple-independent current or voltage sources, etc. The energy applied is a function of the current amplitude and pulse width duration, for example.

In an example, the memory 32 stores different operating modes that are selectable by the operator. For example, the stored operating modes can include instructions for executing a set of modulation parameters associated with a particular treatment site. Different sites can have different associated modulation parameters. Rather than having the operator manually input the modes, the controller 16 can be configured to execute the appropriate instruction based on the selection and/or prescription information from the blockchain, etc. In another example, the memory 32 stores operating modes for different types of treatment (e.g., according to one or more records/entries in a blockchain, etc.). For example, activation can be associated with a different stimulating pressure or frequency range relative to those associated with depressing or blocking tissue function. In a specific example, when the energy application device is an ultrasound transducer, the time-averaged power and peak positive pressure are in the range of 1 mW/cm2-30,000 mW/cm2 and 0.1 MPa to 7 MPa. In another specific example, when the energy application device is a mechanical actuator, the amplitude of vibration is in the range of 0.1 to 10 mm. The selected frequencies may depend on the mode of energy application, e.g., ultrasound or mechanical actuator.

In another example, the memory 32 stores a calibration or setting mode that permits adjustment or modification of the modulation parameters to achieve a desired result. In one example, the stimulation starts at a lower energy parameter and increases incrementally, either automatically or upon receipt of an operator input. As such, an operator can observe the effects as the modulation parameters are being changed.

The system 10 can also include an imaging device that facilitates focusing the energy application device 12. In an example, the imaging device can be integrated with or be implemented as the same device as the energy application device 12 such that different ultrasound parameters (e.g., frequency, aperture, or energy) are applied for targeting and subsequently neuromodulation. In another example, the memory 32 stores a targeting or focusing mode that is used to spatially select the region of interest within an organ or tissue structure. For example, the energy application device 12 can be configured to first operate in the targeting mode to apply energy that is used to capture image data that is used to identify the region of interest. The targeting mode energy is not at levels and/or applied with modulation parameters suitable for preferential activation. However, once the region of interest is identified, the controller 16 can then operate in a treatment mode according to the modulation parameters associated with preferential activation, for example.

The controller 16 can also be configured to receive inputs related to the targeted physiological outcomes as an input to the selection of the modulation parameters. For example, when an imaging modality is used to assess a tissue characteristic, the controller 16 can be configured to receive a calculated index or parameter of the characteristic. Based on whether the index or parameter is above or below a threshold, the modulation parameters can be modified. In an example, the parameter can be a measure of tissue displacement of the affected tissue or a measure of depth of the affected tissue. Further, the energy application device 12 (e.g., an ultrasound transducer) can operate under control of the controller 16 to a) acquire image data to spatially select a region of interest within the target tissue, b) apply the modulating energy to the region of interest, and c) acquire image to determine that the targeted physiological outcome has occurred (e.g., via displacement measurement). In such an example, the imaging device, the assessment device 20 and the energy application device 12 can be the same device.

In another implementation, a successful modulation parameter set can also be stored by the controller 16 (e.g., as an entry or record in a blockchain and/or other distributed ledger, etc.). As such, subject-specific parameters can be determined. Further, the effectiveness of such parameters can be assessed over time. If a particular set of parameters is less effective over time, the subject may be developing insensitivity to activated pathways. If the system 10 includes an assessment device 20, the assessment device 20 can provide feedback to the controller 16. In certain examples, the feedback can be received from a user or an assessment device 20 indicative of a characteristic of the target physiological outcome. The controller 16 can be configured to cause the energy application device 12 to apply the energy according to modulation parameters and to dynamically change the modulation parameters based on the feedback. For example, based on the feedback, the processor 16 can automatically alter the modulation parameters (e.g., the frequency, amplitude, or pulse width of an ultrasound beam or mechanical vibration, etc.).

From the foregoing, it will be appreciated that the above disclosed methods, apparatus, and articles of manufacture have been disclosed and described to implement a distributed ledger managing electronic prescriptions including device prescriptions, pharmaceutical prescriptions, monitoring prescriptions, examination prescriptions, etc. The disclosed methods, apparatus and articles of manufacture improve the operation of a medical information system, insurance system, pharmaceutical system, and/or other computing device by enabling it to quantify, track, pay, and manipulate an electronic prescription construct including patient, device, and action information. The disclosed methods, apparatus and articles of manufacture are accordingly directed to one or more improvement(s) in the functioning of a computer and/or computing device including a management processor, etc. Such improvements are not feasible for humans to do manually and are certainly not mental steps to be conducted in a human mind.

Certain examples provide storage of patient compliance data (e.g., which patient is following a "dose" regimen most closely, etc.) via one or more logical data structures in a distributed ledger. Certain examples provide storage of doctor prescription data (e.g., which doctors are prescribing most effectively, etc.) via one or more logical data structures in a distributed ledger. Certain examples provide storage of effectiveness data (e.g., what was the physiological effect of each given dose, etc.) via one or more logical data structures in a distributed ledger. Certain examples provide storage of hardware/therapy effectiveness (e.g., how well did the machine perform in providing the dose, etc.) via one or more logical data structures in a distributed ledger. Certain examples provide storage of dynamic dosing data (e.g., enable changing of prescriptions based on effectiveness, physiological feedback, etc.) via one or more logical data structures in a distributed ledger.

Certain examples facilitate transaction handling via the distributed ledger. For example, depending on where the therapeutic dose information is being sent and stored, certain examples provide transaction/dosing verification using the distributed ledger. Verification can include using image recognition (e.g., of the patient's internal/external tissue) to verify dose on patient, location, etc. Verification can include using tissue and/or physiological response to verify amplitude or dose of the energy applied, for example. Verification can include using feedback from internal and/or external sensors that measure the energy being applied for verification, for example. Verification can include using other features, such as changes in blood flow or other physiological response, etc., as verification of dosing, for example. In certain examples, verification can include a consensus algorithm (e.g., including use of personal image recognition, etc.) to verify a patient associated with a dose. Therapeutic hardware (e.g., the energy application device 370, etc.) can also be tied to another device (e.g., the cell phone and/or other mobile device 420, etc.) to use global position and/or other biometric data to associate a person with a device and verify dosing.

Associated blockchain and/or other distributed ledger system can be internal (e.g., available to a company associated with a therapeutic device or other medical device, a pharmaceutical company, a healthcare company, etc.) to provide evidence and understanding of use, etc., and/or external (e.g., a therapeutic company can provide dosing data via the distributed ledger to other healthcare players, such as insurance companies, healthcare companies, etc., to allow value to be derived from dosing information, etc.). For example, external value can include driving different patient insurance premiums based on compliance to a prescribed therapeutic regimen, etc. Another value includes different insurance payouts for hospital systems that perform better at diagnosing correct energy application or dosing regimens, for example. These actions/transactions can be added as records and/or used to adjust existing records of a blockchain or other distributed ledger, for example.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
   an energy application device configured to receive energy pulses to be applied to a region of interest of tissue of a patient;
   a pulse generator configured to generate the energy pulses;
   an assessment device configured to provide feedback relating to a target physiological outcome associated with application of the energy pulses to the region of interest of the tissue of the patient; and
   memory including a logical data structure to configure the apparatus according to an energy prescription defining an action to be applied by the energy application device to the region of interest of the patient in accordance with at least one energy application device setting of the energy application device, wherein the action comprises applying the energy pulses to the region of interest of the tissue of the patient via the energy application device, wherein the energy prescription is organized as one or more records in a distributed database and processible by at least one processor to apply the action to the patient, wherein the energy prescription, when processed by the at least one processor, causes the at least one processor to at least:
   automatically alter one or more modulation parameters of the energy application device and the pulse generator based on an energy application mode prescribed by the energy prescription to enable the energy application device and the pulse generator to apply the action to the region of interest of the tissue of the patient using the energy prescription;
   dynamically change at least one energy application device setting of the energy application device based at least in part on the feedback provided by the assessment device;
   communicate with a verification device to verify dynamic dosing data that changes over time in response to the at least one energy application device setting being changed;
   propagate a record of the action to the distributed database, wherein the record comprises the dynamic dosing data;
   modify the energy prescription based on the record; and
   transmit a change to the energy prescription relating to the modification to one or more connected systems.

2. The apparatus of claim 1, wherein the at least one processor is configured to:
   determine payment information associated with the action for the patient; and
   facilitate processing of payment for the action using the payment information when the energy prescription is processed by the energy application device to apply the action to the patient.

3. The apparatus of claim 1, wherein the energy prescription is configured to facilitate processing of payment as the action occurs by the energy application device with respect to the patient.

4. The apparatus of claim 1, wherein modification of the energy prescription by at least one of the energy application device or a second device generates an additional record associated with the energy prescription in the distributed database.

5. The apparatus of claim 1, wherein the target physiological outcome comprises a target physiological outcome of:
   a change in concentration of a molecule of interest in the patient; or
   a change in a characteristic of the molecule of interest in the patient.

6. The apparatus of claim 1, wherein the dynamic dosing data forms a dose log chain organized as one or more energy dosage records in the distributed database, wherein the energy dosage records relate to doses of energy applied to the region of interest of the tissue of the patient.

7. The apparatus of claim 1, wherein the feedback relating to the target physiological outcome relates to effectiveness of application of the energy pulses to the region of interest of the tissue of the patient.

8. The apparatus of claim 1, wherein the one or more connected systems are:
   a manufacturer system associated with a manufacturer of the energy application device, the pulse generator, or the assessment device; and/or
   a beneficiary system providing health-related benefits for the patient.

9. The apparatus of claim 1, wherein the verification device is configured to use image recognition to verify the patient and/or the dynamic dosing data.

10. The apparatus of claim 1, wherein the verification device is configured to measure blood flow and/or physiological response to verify the dynamic dosing data.

11. The apparatus of claim 1, wherein the verification device is configured to measure the energy pulses applied to the region of interest of the tissue of the patient to verify the dynamic dosing data.

12. The apparatus of claim 1, wherein the verification device is a cell phone, a tablet computer, or a smart watch.

13. The apparatus of claim 1, wherein the verification device is configured to detect a global position and/or biometric data to associate the patient with the verification device and to verify the dynamic dosing data.

14. At least one non-transitory computer-readable storage medium including a logical data structure to configure an energy application device according to an energy prescription defining an action to be applied by the energy application device to a region of interest of tissue of a patient in accordance with at least one energy application device setting of the energy application device, wherein the action comprises applying energy pulses to the region of interest of the tissue of the patient via the energy application device, wherein the energy prescription is organized as one or more records in a distributed database and processible by the energy application device to apply the action to the patient and including instructions which, when executed, cause at least one processor to at least:
   automatically alter one or more modulation parameters of the energy application device based on an energy application mode prescribed by the energy prescription to enable the energy application device to apply the action to the region of interest of the tissue of the patient;
   dynamically change at least one energy application device setting of the energy application device based at least in part on feedback provided by an assessment device, wherein the feedback relates to a target physiological outcome associated with application of the energy pulses to the region of interest of the patient communicate with a verification device to verify dynamic dosing data that changes over time in response to the at least one energy application device setting being changed;

propagate a record of the action to the distributed database, wherein the record comprises the dynamic dosing data;

modify the energy prescription based on the record; and transmit a change to the energy prescription relating to the modification to one or more connected systems.

15. The at least one non-transitory computer-readable storage medium of claim 14, wherein the instructions, when executed, cause the at least one processor to:

determine payment information associated with the action for the patient; and facilitate processing of payment for the action using the payment information when the energy prescription is processed by the energy application device to apply the action to the patient.

16. The at least one non-transitory computer-readable storage medium of claim 15, wherein the energy prescription is configured to specify the action to be applied by the energy application device with respect to the patient using the at least one energy application device setting.

17. The at least one non-transitory computer-readable storage medium of claim 14, wherein the energy prescription is configured to facilitate processing of payment as the action occurs by the energy application device with respect to the patient.

18. The at least one non-transitory computer-readable storage medium of claim 14, wherein modification of the energy prescription generates an additional record associated with the energy prescription in the distributed database.

19. A computer-implemented method to configure an energy application device according to an energy prescription defining an action to be applied by the energy application device to a region of interest of tissue of a patient in accordance with at least one energy application device setting of the energy application device, wherein the action comprises applying energy pulses to the region of interest of the tissue of the patient, wherein the energy prescription is organized as one or more records in a distributed database and processible by the energy application device to apply the action to the patient, the method comprising:

automatically altering, using at least one processor, one or more modulation parameters of the energy application device based on an energy application mode prescribed by the energy prescription to enable the energy application device to apply the action to the region of interest of the tissue of the patient;

dynamically changing, using the at least one processor, at least one energy application device setting of the energy application device based at least in part on feedback provided by an assessment device, wherein the feedback relates to a target physiological outcome associated with application of the energy pulses to the region of interest of the patient;

communicating, using the at least one processor, with a verification device to verify dynamic dosing data that changes over time in response to the at least one energy application device setting being changed;

propagating, using the at least one processor, a record of the action to the distributed database, wherein the record comprises the dynamic dosing data;

modifying, using the at least one processor, the energy prescription based on the record; and transmitting, using the at least one processor, a change to the energy prescription relating to the modification to one or more connected systems.

20. The method of claim 19, wherein modification of the energy prescription generates an additional record associated with the energy prescription in the distributed database.

* * * * *